United States Patent [19]

Müller et al.

[11] Patent Number: 5,541,337
[45] Date of Patent: Jul. 30, 1996

[54] SUBSTITUTED 5-ALKOXY-1,2,4-TRIAZOL-3-(THI)ONES

[75] Inventors: Klaus-Helmut Müller, Düsseldorf; Klaus König, Odenthal; Joachim Kluth, Langenfeld; Klaus Lürssen, Bergisch Gladbach; Hans-Joachim Santel, Leverkusen; Robert R. Schmidt, Bergisch Gladbach, all of Germany

[73] Assignee: Bayer Aktiengesellschaft, Leverkusen, Germany

[21] Appl. No.: 269,875

[22] Filed: Jun. 30, 1994

Related U.S. Application Data

[63] Continuation-in-part of Ser. No. 976,185, Nov. 6, 1992, Pat. No. 5,356,865, which is a continuation-in-part of Ser. No. 757,785, Nov. 11, 1991, abandoned, and a continuation-in-part of Ser. No. 48,026, Apr. 15, 1993, abandoned, which is a continuation-in-part of Ser. No. 857,025, Mar. 24, 1992, abandoned, and a continuation-in-part of Ser. No. 31,426, Mar. 15, 1993, Pat. No. 5,405,970, which is a division of Ser. No. 816,365, Dec. 30, 1991, Pat. No. 5,241,074, which is a division of Ser. No. 692,439, Apr. 29, 1991, Pat. No. 5,094,683, which is a division of Ser. No. 556,052, Jul. 20, 1990, Pat. No. 5,057,144, which is a continuation-in-part of Ser. No. 337,775, Apr. 13, 1989, abandoned.

[30] Foreign Application Priority Data

Sep. 22, 1990 [DE] Germany ............................ 40 30 063.3
Apr. 4, 1991 [DE] Germany ............................ 41 10 795.0

[51] Int. Cl.$^6$ .................................................. C07D 249/12
[52] U.S. Cl. ................................................................ 548/263.6
[58] Field of Search ................................................ 548/263.6

[56] References Cited

U.S. PATENT DOCUMENTS 4,948,417  8/1990  Lindig et al. .......................... 71/92
5,057,144  10/1991  Daum et al. .......................... 71/92

FOREIGN PATENT DOCUMENTS 1940367  2/1971  Germany ............................ 548/263.4

OTHER PUBLICATIONS

Zinner et al, "Reaction of Ayanates with, etc." CA 86060X (1975).

Cheng et al, "Reaction of Triazalinediones, etc." J. Org. Chem., 1984, 49, 2917–2922.

*Primary Examiner*—Patricia L. Morris
*Attorney, Agent, or Firm*—Sprung Horn Kramer & Woods

[57] ABSTRACT

Herbicidal 5-alkoxy-1,2,4-triazol-3-(thi)ones of the gerneral formula

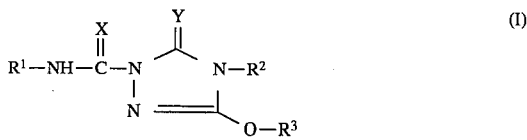

(I)

(in which the radicals $R^1$, $R^2$, $R^3$, X and Y have the meanings given in the description), processes for their preparation, and their use as herbicides, and also new intermediates of the formula (II)

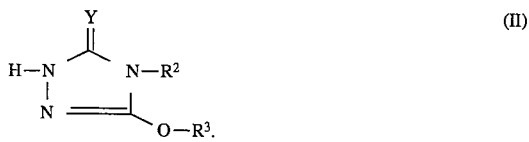

(II)

5 Claims, No Drawings

SUBSTITUTED 5-ALKOXY-1,2,4-TRIAZOL-3-(THI)ONES

This application is a continuation-in-part of application Ser. No. 07/976,185, filed Nov. 6, 1992, now U.S. Pat. No. 5,356,865, which in turn is a continuation-in-part of application Ser. No. 07/757,785, filed Nov. 11, 1991, now abandoned and is a continuation-in-part of application Ser. No. 08/048,026, filed Apr. 15, 1993, now abandoned, which in turn is a continuation-in-part of application Ser. No. 07/857,025, filed on Mar. 24, 1992, now abandoned, and this application further is a continuation-in-part of application Ser. No. 08/031,426, filed Mar. 15, 1993, now U.S. Pat. No. 5,405,970, which is a division of application Ser. No. 07/816,365, filed Dec. 30, 1991, now U.S. Pat. No. 5,241,074, which is a division of application Ser. No. 07/692,439, filed Apr. 29, 1991, now U.S. Pat. No. 5,094,683, which is a division of application Ser. No. 07/556,052, filed on Jul. 20, 1990 now U.S. Pat. No. 5,057,144, which is a continuation-in-part of Application Ser. No. 07/337,775, filed on Apr. 13, 1989, now abandoned.

The invention relates to new substituted 5-alkoxy-1,2,4-triazol-3-(thi)ones, a plurality of several processes, and also new intermediates for their preparation, and their use as herbicides.

This invention also relates to intermediates used to prepare new sulphonylaminocarbonyltriazolinones having substituents bonded via oxygen which possess herbicidal activity. The final products are disclosed in application Ser. No. 08/048,026, filed Apr. 15, 1993 incorporated herein by reference.

It has been disclosed that certain substituted triazolones such as, for example, 4-amino-5-methyl-2-phenylaminocarbonyl-2,4-dihydro-3H-1,2,4-triazol-3-one, have herbicidal properties (cf. EP-A 283,876, EP-A 294,666, EP-A 298,371). However, the herbicidal activity of these compounds is not entirely satisfactory in all fields of application.

Further sulphonylaminocarbonyltriazolinones such as, for example, 2-(2-methoxycarbonyl-phenylsulphonylaminocarbonyl)-4-methyl-5-methoxy-2,4-dihydro-3H-1,2,4-triazol-3-one are the subject of an earlier, but non-prior-published Patent Application (cf. German Patent 3,934,081 dated Dec. 10, 1989).

New substituted 5-alkoxy-1,2,4-triazol-3-(thi)ones of the general formula (I)

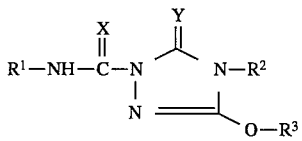

in which

R$^1$ represents alkyl, alkenyl, alkinyl, halogenoalkyl, halogenoalkenyl, halogenoalkinyl, cyanoalkyl, hydroxyalkyl, alkoxyalkyl, alkoximinoalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents alkoxy, alkenyloxy or alkinyloxy, or represents in each case optionally substituted aralkyl, aryloxyalkyl, aralalkenyl, arylalkinyl, aroyl, aryl, aralkyloxy or aryloxy.

R$^2$ represents alkyl, alkenyl, alkinyl, halogenoalkyl, halogenoalkenyl, halogenoalkinyl, alkoxyalkyl, cyanoalkyl, alkoxy, cycloalkyl or cycloalkylalkyl, R$^3$ represents alkyl, alkenyl, alkinyl, halogenoalkyl, halogenoalkenyl, halogenoalkinyl, alkoxyalkyl or cyanoalkyl, X represents oxygen or sulphur and Y represents oxygen or sulphur, have now been found.

Furthermore, it has been found that the new substituted 5-alkoxy-1,2,4-triazol-3-(thi)ones of the general formula (I) are obtained when (a) 5-alkoxy-1,2,4-triazol-3-(thi)ones of the general formula (II)

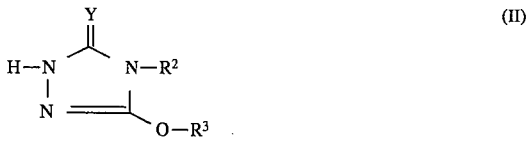

in which

R$^2$, R$^3$ and Y have the abovementioned meaning, are reacted with iso(thio)cyanates of the general formula (III)

in which

R$^1$ and X have the abovementioned meanings, if appropriate in the presence of a diluent and if appropriate in the presence of a basic reaction auxiliary, or when (b) 5-alkoxy-1,2,4-triazol-3-(thi)ones of the general formula (II)

in which

R$^2$, R$^3$ and Y have the abovementioned meaning are reacted with reactive (thio-)carbamates of the general formula (IV)

in which

R$^1$ and X have the abovementioned meanings and

R$^4$ represents alkyl, aralkyl or aryl, if appropriate in the presence of a diluent and if appropriate in the presence of a basic reaction auxiliary, or when (c) 5-alkoxy-1,2,4-triazol-3-(thi)one derivatives of the general formula (V)

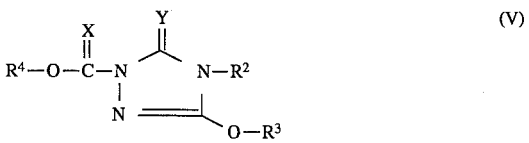

in which

R$^2$, R$^3$, X and Y have the abovementioned meanings and

R$^4$ represents alkyl, aralkyl or aryl, are reacted with amino compounds of the general formula (VI)

in which

R$^1$ has the abovementioned meaning, if appropriate in the presence of a diluent and if appropriate in the presence of a basic reaction auxiliary.

Finally, it has been found that the new substituted 5-alkoxy-1,2,4-triazol-3-(thi)ones of the general formula (I) are distinguished by powerful herbicidal activity.

Surprisingly, the new compounds of the formula (I) show a considerably better herbicidal activity than the compound 4-amino-5-methyl-2-phenylaminocarbonyl-2,4-dihydro-3H-1,2,4-triazol-3-one, which is known.

Additionally, there have been found novel sulphonylaminocarbonyltriazolinones having substitutuents bonded via oxygen, of the general formula (X)

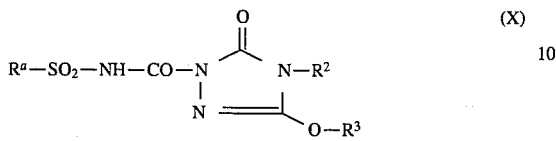

in which $R^2$ represents hydrogen, amino, or an optionally substituted radical from the series comprising alkyl, alkenyl, alkinyl, cycloalkyl, aralkyl, aryl, alkylamino, cycloalkylamino, dialkylamino, $R^3$ represents an optionally substituted radical from the series comprising alkyl, alkenyl, alkinyl, cycloalkyl, cycloalkenyl, aralkyl, aryl, and $R^a$ represents an optionally substituted radical from the series comprising alkyl, aralkyl, aryl, heteroaryl, and salts of compounds of the formula (X), with the exception of 2-(2-methoxycarbonyl-phenylsulphonylaminocarbonyl)-4-methyl-5-methoxy-2,4-dihydro-3H-1,2,4-triazol-3-one (cf. German Patent 3,934,081).

Formula (I) provides a general definition of the substituted 5-alkoxy-1,2,4-triazol-3-(thi)ones according to the invention. Preferred compounds of the formula (I) are those in which $R^1$ represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, each of which has 2 to 8 carbon atoms and 1 to 15 or 13 identical or different halogen atoms, cyanoalkyl having 1 to 8 carbon atoms, hydroxyalkyl having 1 to 8 carbon atoms and 1 to 6 hydroxyl groups, alkoxyalkyl, alkoximinoalkyl, alkoxycarbonylalkyl or alkoxycarbonylalkenyl, each of which has up to 6 carbon atoms in the individual alkyl or alkenyl moieties, alkylaminoalkyl or dialkylaminoalkyl, each of which has 1 to 6 carbon atoms in the individual alkyl moieties, or represents cycloalkyl, cycloalkylalkyl, cycloalkenyl or cycloalkenylalkyl, each of which has 3 to 8 carbon atoms in the cycloalkyl or cycloalkenyl moiety and if appropriate 1 to 6 carbon atoms in the alkyl moiety and each of which is optionally monosubstituted or polysubstituted by identical or different substituents, the following being selected as preferred substituents in the cyclic and optionally in the aliphatic moiety: halogen, cyano, and in each case straight-chain or branched alkyl or halogenoalkyl, each of which has 1 to 4 carbon atoms and if appropriate 1 to 9 identical or different halogen atoms, or in each case divalent alkanediyl or alkenediyl, each of which has up to 4 carbon atoms; $R^1$ furthermore represents heterocyclylalkyl which has 1 to 6 carbon atoms in the straight-chain or branched alkyl moiety and 1 to 9 carbon atoms as well as 1 to 3 hetero atoms—in particular nitrogen, oxygen and/or sulphur—in the heterocyclyl moiety and each of which is optionally monosubstituted or polysubstituted by identical or different substituents, the following being selected as preferred substituents: halogen, cyano, nitro, and in each case straight-chain or branched alkyl, alkoxy, alkylthio, halogenoalkyl, halogenoalkoxy, halogenoalkylthio or alkoxycarbonyl, each of which has 1 to 5 carbon atoms and if appropriate 1 to 9 identical or different halogen atoms; $R^1$ furthermore represents in each case straight-chain or branched alkoxy having 1 to 8 carbon atoms, alkenyloxy having 2 to 8 carbon atoms or alkinyloxy having 2 to 8 carbon atoms, and finally represents aralkyl, aryloxyalkyl, arylalkenyl, arylakinyl, aralkyloxy, aryloxy, aroyl or aryl, each of which has 6 or 10 carbon atoms in the aryl moiety and if appropriate up to 8 carbon atoms in the alkyl, alkenyl or alkinyl moiety, and each of which is optionally monosubstituted or polysubstituted by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which has 1 to 6 carbon atoms and if appropriate 1 to 9 identical or different halogen atoms, cycloalkyl having 3 to 6 carbon atoms and phenoxy, and suitable optional alkyl substituents being: halogen or cyano, $R^2$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl or alkoxy, each of which has 1 to 6 carbon atoms in the individual alkyl moieties, cyanoalkyl having 1 to 8 carbon atoms, or represents cycloalkylalkyl or cycloalkyl, each of which has 3 to 7 carbon atoms in the cycloalkyl moiety and if appropriate 1 to 6 carbon atoms in the straight-chain or branched alkyl moiety, $R^3$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl having 1 to 6 carbon atoms in each of the individual alkyl moieties, or represents cyanoalkyl having 1 to 8 carbon atoms, X represents oxygen or sulphur and Y represents oxygen or sulphur and halogen in the substitution patterns mentioned in the case of $R^1$, $R^2$ and $R^3$ represents fluorine, chlorine, bromine and iodine.

Particularly preferred compounds of the formula (I) are those in which $R^1$ represents methyl, ethyl, n- or i-propyl, n-, i-, s- or t-butyl, in each case straight-chain or branched pentyl, hexyl, heptyl, octyl, nonyl, decyl or dodecyl, or represents allyl, propenyl, n- or i-butenyl, n- or i-pentenyl, n- or i-hexenyl, propargyl, n- or i-butinyl, n- or i-pentinyl, n- or i-hexinyl, or represents straight-chain or branched halogenoalkyl having 1 to 4 carbon atoms and 1 to 9 identical or different halogen atoms, in particular fluorine, chlorine or bromine, or represents in each case straight-chain or branched halogenoalkenyl or halogenoalkinyl, each of which has 3 to 5 carbon atoms and 1 to 3 halogen atoms, in particular fluorine or chlorine, or represents in each case straight-chain or branched cyanoalkyl having 1 to 4 carbon atoms in the alkyl moiety, hydroxyalkyl having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each of which has up to 4 carbon atoms in the individual alkyl or alkenyl moieties, or represents cyclopropyl, cyclopropylmethyl, cyclopropylethyl, cyclobutyl, cyclopentyl, cyclohexyl, cycloheptyl, cyclooctyl, cyclopentylmethyl, cyclohexylmethyl, cyclohexylethyl, cyclohexenyl or cyclohexenylmethyl, each of which is optionally monosubstituted to trisubstituted by identical or different substituents, the following being selected as particularly preferred substituents in the cyclic and if appropriate in the aliphatic moiety: fluorine, chlorine, bromine, methyl, ethyl, n- or i-propyl, n-, i-, s- or t-butyl, cyano, methanediyl, ethanediyl, butanediyl or butadienediyl; $R^1$ furthermore represents heterocyclylinethyl, heterocyclylethyl or heterocyclylpropyl, each of which is optionally monosubstituted to trisubstituted in the heterocyclyl moiety by identical or different substituents, suitable heterocycles in each case being:

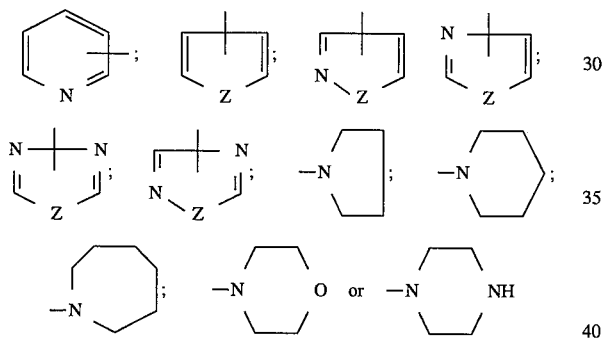

where Z in each case represents oxygen or sulphur and where the following are selected as particularly preferred substituents:

fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; $R^1$ furthermore represents in each case straight-chain or branched alkoxy having 1 to 6 carbon atoms, alkenyloxy having 3 to 6 carbon atoms or alkinyloxy having 3 to 6 carbon atoms, or represents benzyl, phenylethyl, phenylpropyl, phenylbutyl, phenylpentyl, phenylhexyl, phenylheptyl, phenylcyanomethyl, phenylcyanoethyl, phenylcyanopropyl, phenoxymethyl, phenoxyethyl, phenoxypropyl, phenoxybutyl, phenylethinyl, benzyloxy, phenylethyloxy, phenoxy, benzoyl, phenyl or naphthyl, if appropriate straight-chain or branched, each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, difluoromethoxy, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy, $R^2$ represents methyl, ethyl, n- or i-propyl, n-, i-, s- or t-butyl, n- or i-pentyl, n- or i-hexyl, or represents allyl, propargyl, methoxy, ethoxy, methoxymethyl, ethoxymethyl, methoxyethyl or ethoxyethyl, or represents straight-chain or branched halogenoalkyl, halogenoalkenyl and halogenoalkinyl having 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclopentylmethyl, cyclohexylmethyl or cyclohexylethyl, $R^3$ represents methyl, ethyl, n- or i-propyl, n-, i-, s- or t-butyl, n-, i-, s- or t-pentyl, n- or i-hexyl, or represents allyl, propargyl, methoxyethyl, ethoxyethyl, fluoroethyl, chloroethyl, fluoropropyl, chloropropyl or cyanoethyl, X represents oxygen or sulphur and Y represents oxygen or sulphur.

Very particularly preferred compounds of the formula (I) are those in which $R^1$ represents methyl, ethyl, n- or i-propyl, n-, i-, s- or t-butyl, n-, i-, s- or t-pentyl, n-, i-, s- or t-hexyl, propargyl, n- or i-butinyl, n- or i-pentinyl, or represents straight-chain or branched halogenoalkyl having 1 to 4 carbon atoms and 1 to 4 identical or different halogen atoms, in particular fluorine and chlorine, or represents cyanomethyl, cyanoethyl or n- or i-cyanopropyl, or represents cyclopropyl, cyclopropylmethyl, cyclopentyl, cyclopentylmethyl, cyclohexyl or cyclohexylmethyl, each of which is optionally monosubstituted to trisubstituted by identical or different substituents, or represents phenyl, benzyl or phenylethyl, each of which is optionally monosubstituted to trisubstituted by identical or different substituents from the series comprising fluorine, chlorine, bromine, methyl, ethyl and/or trifluoromethyl, or represents in each case straight-chain or branched phenylpropyl, phenylbutyl, phenylpentyl or phenylhexyl, or represents morpholinyl-$C_1$-$C_4$-alkyl, $R^2$ represents methyl, ethyl, n-, i- or cyclopropyl, n-, i-, s- or t-butyl, $R^3$ represents methyl, ethyl, n- or i-propyl, n-, i-, s- or t-butyl, n- or i-pentyl, X represents oxygen and Y represents oxygen.

The new sulphonylaminocarbonyltriazolinones having substituents bonded via oxygen, of the general formula (X), are obtained when (a) triazolinones of the general formula (II)

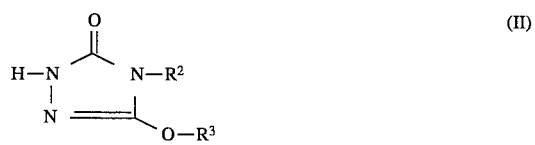

in which $R^2$ and $R^3$ have the abovementioned meanings are reacted with sulphonyl isocyanates of the general formula (XI)

in which $R^a$ has the abovementioned meaning, if appropriate in the presence of a diluent, or when (b) triazolinone derivatives of the general formula (XII)

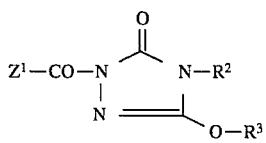

in which

R² and R³ have the abovementioned meanings and

Z¹ represents halogen, alkoxy, aralkoxy or aryloxy, are reacted with sulphonamides of the general formula (XIII)

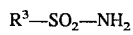

in which $R^a$ has the abovementioned meaning, if appropriate in the presence of an acid acceptor and if appropriate in the presence of a diluent, or when (c) triazolinones of the general formula (II)

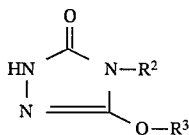

in which

R² and R³ have the abovementioned meanings are reacted with sulphonamide derivatives of the general formula (XIV)

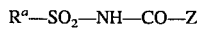

in which $R^a$ has the abovementioned meaning and

Z¹ represents halogen, alkoxy, aralkoxy or aryloxy, if appropriate in the presence of an acid acceptor and if appropriate in the presence of a diluent and, if appropriate, salts are formed, by customary methods, of the compounds of the formula (I) which have been prepared by process (a), (b) or (c).

The new sulphonylaminocarbonyltriazolinones having substituents bonded via oxygen, of the general formula (I), and their salts are distinguished by a powerful herbicidal activity.

Surprisingly, the new compounds of the formula (X) show a considerably better herbicidal action than the known compound 2-(2-chlorophenylsulphonylaminocarbonyl)-4,5-dimethyl-2,4-dihydro-3H-1,2,4-triazol-3-one, which has a similar structure.

The invention preferably relates to compounds of the formula (X) in which

R² represents hydrogen, amino, or represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, or represents $C_3$–$C_6$-alkenyl or $C_3C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxycarbonyl, or represents $C_1$–$C_4$-alkylamino which is optionally substituted by fluorine, cyano, $C_1$–$C_4$-alkoxy or $C_1$–$C_4$-alkoxy-carbonyl, or represents $C_3$–$C_6$-cycloalkylamino or di-($C_1$–$C_4$-alkyl)-amino, R³ represents $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxycarbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkyl-sulphinyl, $C_1$–$C_4$-alkylsulphonyl and/or $C_1$–$C_4$-alkoxy-carbonyl, and $R^a$ represents the group

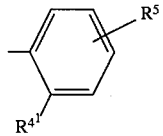

in which $R^{4'}$ and R⁵ are identical or different and represent hydrogen, fluorine, chlorine, bromine, iodine, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_4$-alkyl) amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di- ($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxycarbonyl, carboxyl or phenyl), or represent $C_2$–$C_6$-alkinyl (which is optionally substituted by fluorine, chlorine, bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$C_4$-alkylsulphinyl or $C_1$–$C_4$-alkylsulphonyl), or represent $C_1$–$C_4$-alkylthio (which is optionally substituted by fluorine, chlorine, bromine, cyano, carboxyl, $C_1$–$C_4$-alkoxycarbonyl, $C_1$–$C_4$-alkylthio, $C_1$–$C_4$-alkylsulphinyl or $C_1$–$C_4$-alkylsulphonyl), or represent $C_3$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxycarbonyl), $C_3$–$C_6$-alkinyloxy, $C_3$–$C_6$-alkinylthio or the radical $—S(O)_p—R^6$ where p represents the numbers 1 or 2 and $R^6$ represents $C_1$–$C_4$-alkyl (which is optionally substituted by fluorine, chlorine, bromine, cyano or $C_1$–$C_4$-alkoxy-carbonyl), $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino, phenyl or the radical —$NHOR^7$ where $R^7$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl), or represents $C_3$–$C_6$-alkenyl (which is optionally substituted by fluorine, chlorine or bromine),$C_3$–$C_6$-alkinyl, $C_3$–$C_6$-cycloalkyl, $C_3$–$C_6$-cycloalkyl-$C_1$–$C_2$-alkyl, phenyl-$C_1$–$C_2$-alkyl (which is optionally substituted by fluorine, chlorine, nitro, cyano, $C_1$–$C_4$-alkyl, $C_1$–$C_4$-alkoxy or $C_1$–$C_4$-alkoxy-carbonyl), or represents benzhydryl, or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), $R^{4^1}$ and/or $R^5$ furthermore represent phenyl or phenoxy, or represent $C_1$–$C_4$-alkylcarbonylamino, $C_1$–$C_4$-alkoxy-carbonylamino, $C_1$–$C_4$-alkylamino-carbonyl-amino, di-($C_1$–$C_4$-alkyl)-amino-carbonylamino, or the radical —CO—$R^8$ where $R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)-amino (which are optionally substituted by fluorine and/or chlorine), $R^{4^1}$ and/or $R^5$ furthermore represent trimethylsilyl, thiazolinyl, $C_1$–$C_4$-alkylsulphonyloxy, di-($C_1$–$C_4$-alkyl)aminosulphonylamino or the radical —CH=N—$R^9$ where $R^9$ represents $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, or represents benzyl which is optionally substituted by fluorine or chlorine, or represents $C_3$–$C_6$-alkenyl or $C_3$–$C_6$-alkinyl, each of which is optionally substituted by fluorine or chlorine, or represents phenyl which is optionally substituted by fluorine, chlorine, bromine, $C_1$–$C_4$-alkyl, $C_1$–$C_4$-alkoxy, trifluoromethyl, trifluoromethoxy or trifluoromethylthio, or represents optionally fluorine- and/or chlorine-substituted $C_1$–$C_6$-alkoxy, $C_3$–$C_6$-alkenoxy, $C_3$–$C_6$-alkinoxy or benzyloxy, or represents amino, $C_1$–$C_4$-alkylamino, di-($C_1$–$C_4$-alkyl)-amino, phenylamino, $C_1$–$C_4$-alkyl-carbonyl-amino, $C_1$–$C_4$-alkoxy-carbonylamino or $C_1$–$C_4$-alkyl-sulphonylamino, or represents phenylsulphonylamino which is optionally substituted by fluorine, chlorine, bromine or methyl, furthermore $R^a$ represents the radical

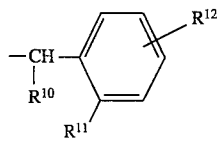

where $R^{10}$ represents hydrogen or $C_1$–$C_4$-alkyl, $R^{11}$ and $R^{12}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), carboxyl, $C_1$–$C_4$-alkoxy-carbonyl, dimethylaminocarbonyl, $C_1$–$C_4$-alkylsulphonyl or di-($C_1$–$C_4$-alkyl) -aminosulphonyl;

furthermore $R^a$ represents the radical

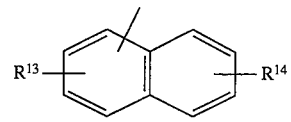

where $R^{13}$ and $R^{14}$ are identical or different and represent hydrogen, fluorine, chlorine, bromine, nitro, cyano, $C_1$–$C_4$-alkyl (which is optionally substituted by fluorine and/or chlorine) or $C_1$–$C_4$-alkoxy (which is optionally substituted by fluorine and/or chlorine);

furthermore $R^a$ represents the radical

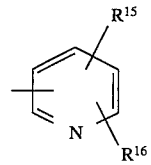

where $R^{15}$ and $R^{16}$ are identical or different and represent hydrogen, fluorine, chlorine, bromine, nitro, cyano, $C_1$–$C_4$-alkyl (which is optionally substituted by fluorine and/or chlorine), $C_1$–$C_4$-alkoxy (which is optionally substituted by fluorine and/or chlorine), or represent $C_1$–$C_4$-alkylthio, $C_1$–$C_4$-alkylsulphinyl or $C_1$–$C_4$-alkylsulphonyl (which are optionally substituted by fluorine and/or chlorine), or represent aminosulphonyl, mono-($C_1$–$C_4$-alkyl)-aminosulphonyl, di-($C_1$–$C_4$-alkyl)-aminosulphonyl or $C_1$–$C_4$-alkoxycarbonyl or dimethylaminocarbonyl;

furthermore $R^a$ represents the radical

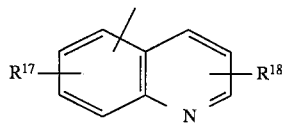

where $R^{17}$ and $R^{18}$ are identical or different and represent hydrogen, fluorine, chlorine, bromine, $C_1$–$C_4$-alkyl (which is optionally substituted by fluorine and/or bromine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (which are optionally substituted by fluorine and/or chlorine), or represent di-($C_1$–$C_4$-alkyl)-aminosulphonyl;

furthermore $R^a$ represents the radical

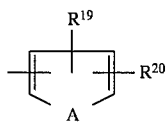

where $R^{19}$ and $R^{20}$ are identical or different and represent hydrogen, fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (which is optionally substituted by fluorine and/or chlorine), di-($C_1$–$C_4$-alkyl)-amino-sulphonyl, $C_1$–$C_4$-alkoxy-carbonyl or dimethylaminocarbonyl, and A represents oxygen, sulphur or the group N—$Z^1$, where $Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkylcarbonyl, $C_1$–$C_4$-alkoxy-carbonyl or di-($C_1$–$C_4$-alkyl)-aminocarbonyl;

furthermore $R^a$ represents the radical

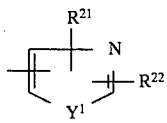

where $R^{21}$ and $R^{22}$ are identical or different and represent hydrogen, $C_1$–$C_4$-alkyl, halogen, $C_1$–$C_4$-alkoxycarbonyl, $C_1$–$C_4$-alkoxy or $C_1$–$C_4$-halogenoalkoxy, $Y^1$ represents sulphur or the group N—$R^{23}$, where $R^{23}$ represents hydrogen or $C_1$–$C_4$-alkyl;

furthermore $R^a$ represents the radical

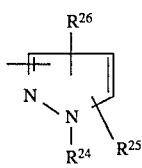

where $R^{24}$ represents hydrogen, $C_1$–$C_4$-alkyl, benzyl, pyridyl, quinolinyl or phenyl, $R^{25}$ represents hydrogen, halogen, cyano, nitro, $C_1$–$C_4$-alkyl (which is optionally substituted by fluorine and/or chlorine), $C_1$–$C_4$-alkoxy (which is optionally substituted by fluorine and/or chlorine), dioxolanyl or $C_1$–$C_4$-alkoxy-carbonyl and $R^{26}$ represents hydrogen, halogen or $C_1$–$C_4$-alkyl;

furthermore $R^a$ represents one of the groups listed below

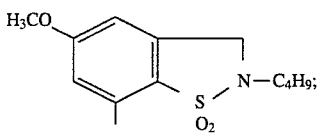

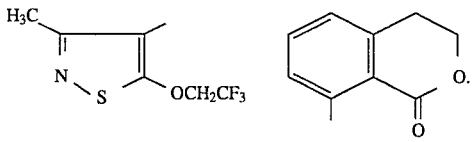

The invention furthermore preferably relates to the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of compounds of the formula (I) in which $R^1$, $R^2$ and $R^3$ have the meanings mentioned above as being preferred.

In particular, the invention relates to compounds of the formula (X) in which $R^2$ represents hydrogen, amino, $C_1$–$C_4$-alkyl which is optionally substituted by fluorine, cyano, methoxy or ethoxy, or represents allyl, $C_3$–$C_6$-cycloalkyl, benzyl, phenyl, $C_1$–$C_3$-alkylamino, $C_3$–$C_6$-cycloalkylamino or di-($C_1$–$C_3$-alkyl)-amino, $R^3$ represents $C_1$–$C_4$-alkyl which is optionally substituted by fluorine and/or chlorine, methoxy or ethoxy, or represents $C_3$–$C_4$-alkenyl which is optionally substituted by fluorine and/or chlorine, or represents $C_3$–$C_6$-cycloalkyl, or represents benzyl which is optionally substituted by fluorine, chlorine and/or methyl, and $R^a$ represents the group

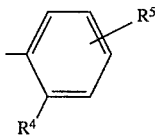

where $R^{4'}$ represents fluorine, chlorine, bromine, methyl, trifluoromethyl, methoxy, difluoromethoxy, trifluoromethoxy, 2-chloro-ethoxy, 2-methoxyethoxy, $C_1$–$C_3$-alkylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, methoxyaminosulphonyl, phenyl, phenoxy or $C_1$–$C_3$-alkoxy-carbonyl and $R^5$ represents hydrogen, fluorine, chlorine or bromine;

furthermore $R^a$ represents the radical

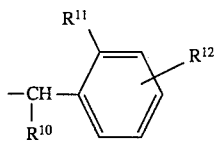

where $R^{10}$ represents hydrogen, $R^{11}$ represents fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl and $R^{12}$ represents hydrogen;
furthermore
$R^a$ represents the radical

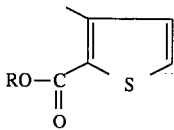

where R represents $C_1$–$C_4$-alkyl, or represents the radical

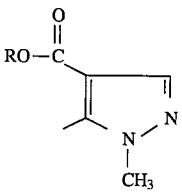

where R represents $C_1$–$C_4$-alkyl.

The abovementioned definitions of radicals, in general or mentioned in preferred ranges, can be combined with each other in any desired way, that is to say also between the particular preferred ranges.

Examples of the compounds of the formula (I) according to the invention are listed in Table 1 below.

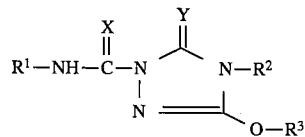

(I)

TABLE 1

| Examples of the compounds of the formula (I) | | | | |
|---|---|---|---|---|
| $R^1$ | $R^2$ | $R^3$ | X | Y |
| i-$C_3H_7$ | $CH_3$ | $CH_3$ | O | O |
| $CF_3$—C($CH_3$)$_2$— | $CH_3$ | $C_2H_5$ | O | O |
| F—$CH_2$—C($CH_3$)$_2$— | $CH_3$ | $C_2H_5$ | O | O |
| $C_2H_5$—C($CH_3$)$_2$— | $CH_3$ | $CH_3$ | O | O |
| $C_3H_7$—C($CH_3$)$_2$— | $CH_3$ | $CH_3$ | O | O |
| i-$C_3H_7$—C($CH_3$)$_2$— | $CH_3$ | $CH_3$ | O | O |
| ⟨phenyl⟩—C($CH_3$)$_2$— | $CH_3$ | $CH_3$ | O | O |
| ⟨phenyl⟩—$CH_2$—C($CH_3$)$_2$— | $CH_3$ | $CH_3$ | O | O |
| ⟨phenyl⟩—($CH_2$)$_2$—C($CH_3$)$_2$— | $CH_3$ | $CH_3$ | O | O |
| ⟨phenyl⟩—($CH_2$)$_2$—C($CH_3$)$_2$— | $CH_3$ | $CH_3$ | O | O |
| ⟨phenyl⟩—$CH_2$—C($CH_3$)$_2$— | $CH_3$ | $CH_3$ | O | O |
| ⟨phenyl⟩—CH($CH_3$)— | $CH_3$ | $CH_3$ | O | O |
| ⟨phenyl⟩—C($CH_3$)$_2$— | $CH_3$ | $C_2H_5$ | O | O |
| $CH_3O$—⟨phenyl⟩—$CH_2$—$CH_2$—C($CH_3$)$_2$— | $CH_3$ | $CH_3$ | O | O |

If, for example, 5-ethoxy-4-ethyl-2,4-dihydro-3H-1,2,4-triazole-3-thione and isopropyl-isocyanate are used as starting substances, the course of the reaction of process (a) according to the invention can be illustrated by the following equation:

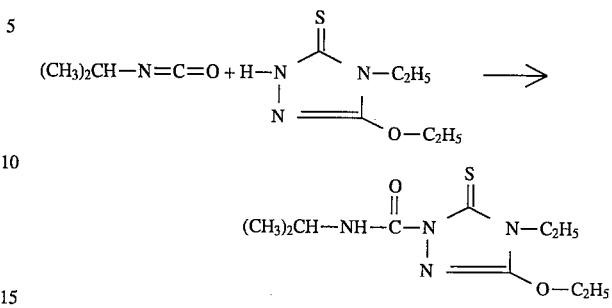

If, for example, 5-isopropoxy-4-methyl-2,4-dihydro-3H-1,2,4-triazol-3-one and O-Methyl-N-tert.-butylthiocarbamate are used as starting substances, the course of the reaction of process (b) according to the invention can be illustrated by the following equation:

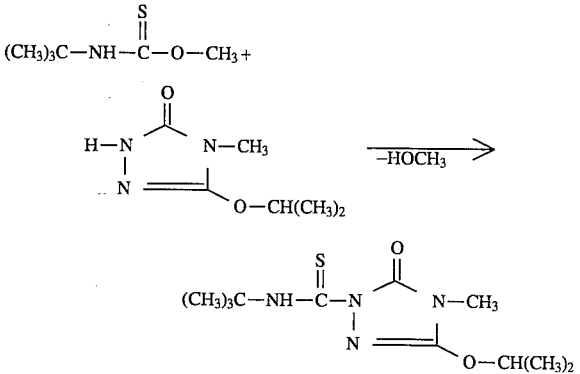

If, for example, 4-isopropyl-5-methoxy-2-phenoxycarbonyl-2,4-dihydro-3H-1,2,4-triazol-3-one and cyclohexylamine are used as starting substances, the course of the reaction of process (c) according to the invention can be illustrated by the following equation:

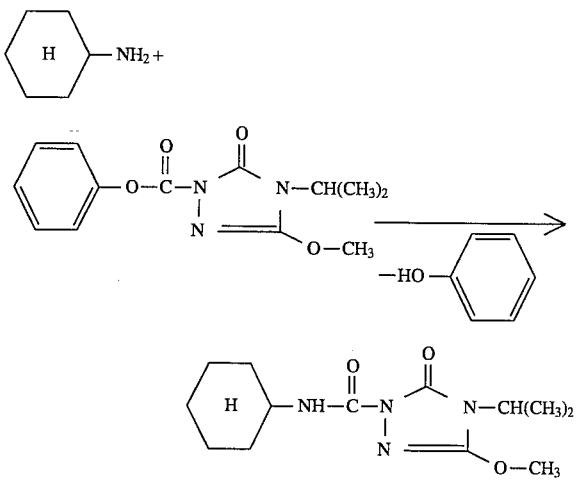

Formula (II) provides a general definition of the 5-alkoxy-1,2,4-triazol-3-(thi)ones to be used as starting substances in processes (a) and (b) according to the invention for the preparation of compounds of the formula (I).

In formula (II), $R^2$, $R^3$ and Y preferably, or in particular, have those meanings which have already been mentioned above in connection with the description of the compounds of the formula (I) according to the invention as being preferred, or as particularly preferred, for $R^2$, $R^3$ and Y.

Examples of the compounds of formula X are listed in Table 2 below—cf. also the Preparation Examples

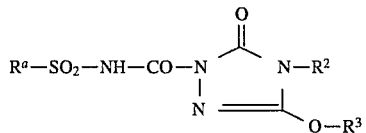
(X)

TABLE 2

Examples of the compounds of the formula (X)

| $R^2$ | $R^3$ | $R^a$ |
|---|---|---|
| cyclopropyl | $CH_3$ | 2-F-phenyl |
| cyclopropyl | $CH_3$ | 2-Cl-phenyl |
| $CH_3$ | $C_2H_5$ | 2-$COOC_2H_5$-phenyl |
| $CH_3$ | $CH_2-CH=CH_2$ | 2-$OCHF_2$-phenyl |
| $CH_3$ | $CH_3$ | 2-$SO_2N(CH_3)_2$-phenyl |
| $CH_3$ | $CH_3$ | 2-$COOCH_3$-benzyl |
| $CH_3$ | $C_2H_5$ | 4-$COOC_2H_5$-1-methylpyrazol-5-yl |
| $CH_3$ | $C_2H_5$ | 3-$COOCH_3$-thien-2-yl |

TABLE 2-continued

Examples of the compounds of the formula (X)

| R² | R³ | Rᵃ |
|---|---|---|
| CH₃ | C₂H₅ | 2-biphenyl |
| C₂H₅ | C₂H₅ | 2-phenoxyphenyl |
| C₂H₅ | C₃H₇ | 3-CF₃-2-pyridyl |
| cyclopropyl | CH₃ | 2-(OCF₃)benzyl |
| cyclopropyl | C₂H₅ | 2-(OCH₂CH₂Cl)phenyl |
| cyclopropyl | CH(CH₃)₂ | 3-CON(CH₃)₂-2-pyridyl |
| CH₃ | CH(CH₃)₂ | 3-SO₂NH₂-2-pyridyl |
| CH₃ | CH₂—CH=CH₂ | 2-SCH(CH₃)₂-phenyl |
| C₂H₅ | CH₃ | 2-SO₂CH₃-phenyl |
| C₂H₅ | C₂H₅ | 2-F-phenyl |

TABLE 2-continued

Examples of the compounds of the formula (X)

| R² | R³ | Rᵃ |
|---|---|---|
| CH₃ | C₂H₅ | 2-Si(CH₃)₃-phenyl |
| C₂H₅ | C₃H₇ | 2-OCF₃-benzyl |
| CH₂ | C₂H₅ | 2-methyl-3-CON(CH₃)₂-pyridinyl |
| CH₂-phenyl | CH₃ | 2-Br-phenyl |
| cyclopropyl | C₂H₅ | 2-(OCH₂CH₂—OCH₃)-phenyl |
| cyclobutyl | CH₃ | 4-Br-1,5-dimethyl-pyrazol-3-yl |
| cyclopentyl | C₂H₅ | 2-SO₂N(CH₃)₂-phenyl |
| cyclohexyl (H) | C₃H₇-n | 2-OCHF₂-benzyl |
| CH₃ | C₂H₅ | 2-COOCH(CH₃)₂-4-Cl-phenyl |
| CH₃ | CH₃ | 2-COOC₂H₅-4-(F₂CHO)-phenyl |

TABLE 2-continued

Examples of the compounds of the formula (X)

| R² | R³ | Rᵃ |
|---|---|---|
| CH₃ | C₂H₅ | 2-phenoxyphenyl |
| CH₃ | S—CH₂—C≡CH | 2-(thiazol-2-yl)phenyl |
| CH₃ | C₂H₅ | 2-(OCH₂CF₃)phenyl |
| cyclopropyl | C₂H₅ | 1-phenyl-5-methyl-4-(COOCH₃)-pyrazol-3-yl |
| cyclopropyl | CH₃ | 1-(isoquinolin-1-yl)-5-methyl-4-(COOCH₃)-pyrazol-3-yl |
| CH₃ | CH₃ | 4-chloro-5-methyl-isothiazol-3-yl |
| CH₃ | C₃H₇ | 2,6-dimethyl-3-(CON(CH₃)₂)-pyridin-4-yl |
| C₂H₅ | C₂H₅ | 3-(COOCH₃)-thien-2-yl |
| CH₂—CH=CH₂ | C₂H₅ | 2-(COOCH₃)benzyl |

TABLE 2-continued

Examples of the compounds of the formula (X)

| $R^2$ | $R^3$ | $R^a$ |
|---|---|---|
| $CH_2-CH=CH_2$ | $CH_3$ | 4-bromo-1,5-dimethyl-pyrazol-3-yl |
| $C_2H_5$ | $CH_3$ | 2-(COOCH$_3$)phenyl |
| $C_2H_5$ | $C_2H_5$ | 2-[SO$_2$NCH$_3$(OCH$_3$)]phenyl |
| $C_3H_7$ | $CH_2-CH=CH_2$ | 2-methylphenyl |
| $CH_3$ | $CH_3$ | 2-(OCH$_3$)phenyl |
| cyclopropyl | $C_2H_5$ | 2-chloro-6-methylphenyl |
| cyclopropyl | $C_2H_5$ | 2-bromo-6-methylphenyl |
| $C_2H_5$ | $C_2H_5$ | 4-chloro-1,5-dimethyl-pyrazol-3-yl |
| $CH_3$ | $C_2H_5$ | 2-(SO$_2$-phenyl)phenyl |

TABLE 2-continued

Examples of the compounds of the formula (X)

| R² | R³ | Rᵃ |
|---|---|---|
| CH₃ | C₃H₇ | 2-(OCHF₂)-C₆H₄-CH₂- |
| C₃H₇ | CH₃ | 3-methyl-2-(COOCH₃)-thiophene |
| C₃H₇ | CH₃ | 2-(OCH₃)-C₆H₄- |
| C₃H₇ | C₂H₅ | 2-(OCH₂CH₂-Cl)-C₆H₄- |
| C₃H₇ | C₂H₅ | 2-F-C₆H₄- |
| CH₃ | C₂H₅ | 2-(oxazolyl)-C₆H₄- |
| CH₃ | CH₃ | 3-(CF₃)-2-pyridyl |
| N(CH₃)₂ | CH₃ | 2-naphthyl |
| CH₃ | C₂H₅ | 3-(SO₂NH₂)-2-pyridyl |
| C₂H₅ | C₂H₅ | 3-(SO₂NH₂)-2-pyridyl |
| cyclopropyl | CH₃ | 3-(SO₂NH₂)-2-pyridyl |

TABLE 2-continued

Examples of the compounds of the formula (X)

| R² | R³ | Rᵃ |
|---|---|---|
| CH₃ | C₂H₅ | (thiophene)—O—CF₂—CF₂Cl |
| N(CH₃)₂ | CH₃ | OCH₂CH₂—Cl (phenyl) |

If, for example, 2,6-difluoro-phenylsulphonyl isocyanate and 5-ethoxy-4-methyl-2,4-dihydro-3H-1,2,4-triazol-3-one are used as starting substances, the course of the reaction in process (a) according to the invention can be outlined by the following equation:

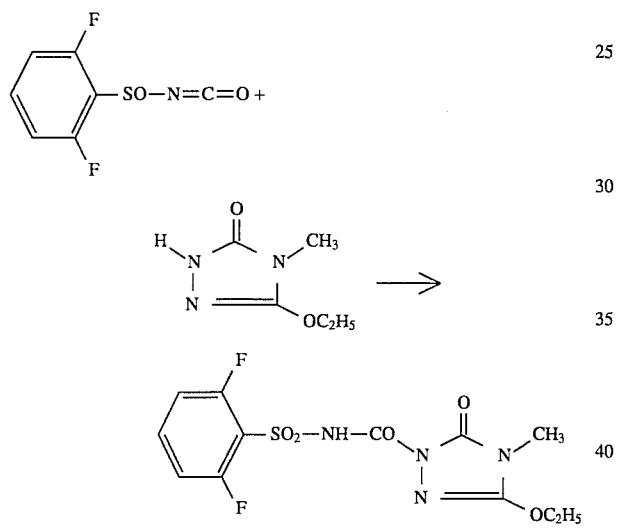

If, for example, 2-methylthio-benzenesulphonamide and 2-chlorocarbonyl-4-dimethylamino-5-propyloxy-2,4-dihydro-3H-1,2,4-triazol-3-one are used as starting substances, the course of the reaction in process (b) according to the invention can be outlined by the following equation:

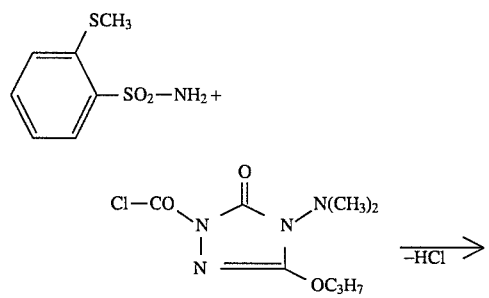

-continued

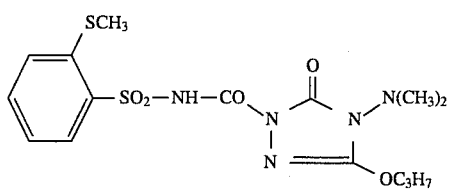

If, for example, N-methoxycarbonyl-2-methoxy-benzenesulphonamide and 5-methoxy-4-difluoromethyl-2,4-dihydro-3H-1,2,4-triazol-3-one are used as starting substances, the course of the reaction in process (c) according to the invention can be outlined by the following equation:

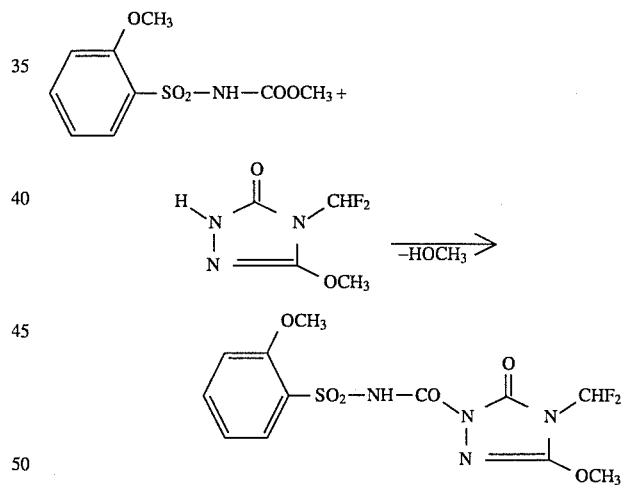

Formula (II) provides a general definition of the triazolinones to be used as starting substances in processes (a) and (c) according to the invention for the preparation of compounds of the formula (X).

In formula (II), $R^2$ and $R^3$ preferably, or in particular, have those meanings which have already been mentioned above in connection with the description of the compounds of the formula (X) according to the invention as being preferred, or particularly preferred, for $R^2$ and $R^3$.

Examples of the starting substances of the formula (II) are listed in Table 3 below.

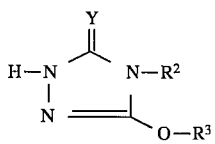
(II)

TABLE 2

Examples of the starting substances of the formula (II)

| $R^2$ | $R^3$ | Y |
|---|---|---|
| $CH_3$ | $CH_3$ | O |
| $CH_3$ | $CH_3$ | S |
| $CH_3$ | $C_2H_5$ | O |
| $CH_3$ | $C_2H_5$ | S |
| $CH_3$ | $C_3H_7$ | O |
| $CH_3$ | $C_3H_7$ | S |
| $CH_3$ | $CH(CH_3)_2$ | O |
| $CH_3$ | $CH(CH_3)_2$ | S |
| $CH_3$ | $-CH_2-CH=CH_2$ | O |
| $CH_3$ | $-CH_2-CH=CH_2$ | S |
| $C_2H_5$ | $CH_3$ | O |
| $C_2H_5$ | $CH_3$ | S |
| $C_2H_5$ | $C_2H_5$ | O |
| $C_2H_5$ | $C_2H_5$ | S |
| $C_2H_5$ | $CH(CH_3)_2$ | O |
| $C_2H_5$ | $-CH_2-CH=CH_2$ | O |
| $C_2H_5$ | $CH(CH_3)_2$ | S |
| $C_2H_5$ | $-CH_2-CH=CH_2$ | S |

TABLE 3

Examples of the starting substances of the formula (II)

| $R^2$ | $R^3$ | Y |
|---|---|---|
| H | $CH_3$ | O |
| $CH_3$ | $CH_3$ | O |
| $C_2H_5$ | $CH_3$ | O |
| $C_3H_7$ | $CH_3$ | O |
| $CH(CH_3)_2$ | $CH_3$ | O |
| $C_4H_9$ | $CH_3$ | O |
| cyclopropyl | $CH_3$ | O |
| $CH_3$ | $CH_2$-phenyl | O |
| $CH_3$ | $CH_2-C\equiv CH$ | O |
| $C_3H_7$ | $C_2H_5$ | O |
| cyclopropyl | $C_2H_5$ | O |
| $CH_2-CH=CH_2$ | $C_2H_5$ | O |
| $CH_2-CHBr-CH_2Br$ | $C_2H_5$ | O |
| cyclopropyl | $C_3H_7$ | O |
| cyclopropyl | $CH_2-CH=CH_2$ | O |
| cyclopropyl | $CH(CH_3)_2$ | O |
| $C_3H_7$ | $CH(CH_3)_2$ | O |
| $CH_2-CH=CH_2$ | $C_3H_7$ | O |
| $C_2H_5$ | $C_3H_7$ | O |

TABLE 3-continued

Examples of the starting substances of the formula (II)

| $R^2$ | $R^3$ | Y |
|---|---|---|
| $C_2H_5$ | $-CH_2-C\equiv CH$ | O |
| $C_3H_7$ | $C_3H_7$ | O |

The starting substances of the formula (II) are known in some cases (cf. J. Chem. Soc C 1967, 2700–2704; J. Heterocycl. Chem. 15 (1978), 377–384) subject of an earlier, but non-prior-published, Patent Application (cf. German Patent 4,030,063, dated Those compounds of the general formula (II) in which Y represents oxygen and $R^2$ and $R^3$ have the abovementioned meanings are new and are a subject of the present patent application.

The new 5-alkoxy-1,2,4-triazol-3-ones (II, Y=O) are obtained when hydrazinoformic esters of the general formula (VII)

$$H_2N-NH-CO-O-R^4 \qquad (VII)$$

in which $R^4$ has the abovementioned meaning are reacted with alkyliminocarboxylic diesters of the general formula (VIII)

in which $R^2$ and $R^3$ have the abovementioned meaning, if appropriate in the presence of a diluent such as, for example, o-dichlorobenzene, at temperatures between 0° C. and 200° C., preferably between 50° C. and 150° C. (cf. the Preparation Examples).

The starting substances of the formulae (VII) and (VIII) are known chemicals.

Formula (III) provides the general definition of the iso(thio)cyanates to be used as starting substances in process (a) according to the invention for the preparation of compounds of the formula (I).

In formula (III), $R^1$ and X preferably, or in particular, have those meanings which have already been mentioned above in connection with the description of the compounds of the formula (I) according to the invention as being preferred, or as particularly preferred, for $R^1$ and X.

The starting substances of the formula (III) are known chemicals for organic synthesis.

Formula (IV) provides a general definition of the reactive (thio)carbamates to be used as starting substances in process (b) according to the invention for the preparation of compounds of the formula (I).

In formula (IV), $R^1$ and X preferably, or in particular, have those meanings which have already been mentioned above in connection with the description of the compounds of the formula (I) according to the invention as being preferred, or as particularly preferred, for $R^1$ and X;

$R^4$ preferably represents methyl, ethyl, phenyl or benzyl.

The starting substances of the formula (IV) are known chemicals for organic synthesis.

Formula (V) provides a general definition of the 5-alkoxy-1,2,4-triazol-3-(thi)one derivatives to be used as starting substances in process (c) according to the invention for the preparation of compounds of the formula (I).

In formula (V), $R^2$, $R^3$, X and Y preferably, or in particular, have those meanings which have already been mentioned above in connection with the description of the compounds of the formula (I) according to the invention as being preferred, or as particularly preferred, for $R^2$, $R^3$, X and Y;

$R^4$ preferably represents methyl, ethyl, phenyl or benzyl.

The starting substances of the formula (V) were hitherto not known from the literature and are a subject of the present patent application.

The new 5-alkoxy-1,2,4-triazol-3-(thi)one derivatives of the general formula (V) are obtained when 5-alkoxy-1,2,4-triazol-3-(thi)ones of the general formula (II)

$$\underset{\underset{N}{\overset{H-N}{|}}}{\overset{Y}{\|}}\underset{O-R^3}{\overset{N-R^2}{\diagup}} \quad (II)$$

in which $R^2$, $R^3$ and Y have the abovementioned meanings are reacted with chloro(thio)formic esters of the general formula (IX)

$$R^4-O-\overset{\overset{X}{\|}}{C}-Cl \quad (IX)$$

in which $R^4$ and X have the abovementioned meanings, if appropriate in the presence of a diluent such as, for example, tetrahydrofuran, and if appropriate in the presence of an acid acceptor such as, for example, potassium tert-butylate, at temperatures between −20° C. and +100° C.

Formula (VI) provides a general definition of the amino compounds furthermore to be used as starting substances in process (c) according to the invention for the preparation of compounds of the formula (I).

In formula (VI), $R^1$ preferably, or in particular, has the meaning which has already been mentioned above in connection with the description of the compounds of the formula (I) according to the invention as being preferred, or as particularly preferred, for $R^1$.

The starting substances of the formula (VI) are known chemicals for organic synthesis.

Processes (a), (b) and (c) according to the invention for the preparation of the new compounds of the formula (I) are preferably carried out in each case using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

If appropriate, processes (a), (b) and (c) according to the invention are in each case carried out in the presence of a basic reaction auxiliary. Suitable substances which are employed are preferably basic organic nitrogen compounds. These include, for example, trimethylamine, triethylamine, tripropylamine, tributylamine, diisopropylamine, dicyclohexylamine, N,N-dimethylaniline, N,N-dimethylbenzylamine, pyridine, 4-dimethylamino-pyridine, 1,5-diazabicyclo-(4,3,0]-non-5-ene (DBN), 1,8-diazabicyclo[5,4,0)-undec-7-ene (DBU) and 1,4-diazabicyclo-[2,2,2]-octane (DABCO).

When carrying out processes (a), (b) and (c) according to the invention, the reaction temperatures can be varied in each case in a substantial range. In general, the processes are carried out at temperatures between −20° C. and 150° C., preferably at temperatures between 0° C. and 100° C.

In general, processes (a), (b) and (c) according to the invention are carried out under atmospheric pressure. However, it is also possible to carry out the processes under increased or reduced pressure.

For carrying out processes (a), (b) and (c) according to the invention, the starting substances required in each case are generally employed in approximately equimolar amounts. However, it is also possible to use one of the two components employed in each case in a larger excess. In general, the reactions are carried out in a suitable diluent in the presence of a basic reaction auxiliary, and the reaction mixture is stirred for several hours at the particular temperature required. Working-up in the processes according to the invention is carried out in each case by customary methods.

The compounds of the general formula (II) which are used to prepare components of formula X in which $R^2$ has the abovementioned meaning and $R^3$ represents in each case optionally substituted cycloalkyl, cycloalkenyl, aralkyl or aryl, are new and a subject of the present patent application.

The compounds of the formula (II) are obtained when hydrazinoformic esters of the general formula (XV)

$$H_2N-NH-CO-O-R^{4^1} \quad (XV)$$

in which $R^{4^1}$ has the abovementioned meaning are reacted with alkyliminocarbonic diesters of the general formula (XVI)

$$R^2-N=C\underset{O-R^3}{\overset{O-R^3}{\diagup}} \quad (XVI)$$

in which $R^2$ and $R^3$ have the abovementioned meaning, if appropriate in the presence of a diluent such as, for example, methanol, at temperatures between 0° C. and 50° C., and the compounds formed in this process, of the general formula (XVII)

$$R^{4^1}-O-CO-NH-N=C\underset{NH-R^2}{\overset{O-R^3}{\diagup}} \quad (XVII)$$

in which $R^2$, $R^3$ and $R^{4^1}$ have the abovementioned meaning, are, if appropriate, isolated by customary methods and heated to temperatures between 50° C. and 150° C., if appropriate in the presence of a diluent such as, for example, toluene, xylene or o-dichlorobenzene (cf. Preparation Examples).

The starting substances of the formulae (XV) and (XVI) are known chemicals.

The intermediates of the formula (XVII) are new compounds.

Formula (XI) provides a general definition of the sulphonyl isocyanates furthermore to be used as starting substances in process (a) according to the invention for the preparation of compounds of the formula (X).

In formula (XI), $R^a$ preferably, or in particular, has that meaning which has already been mentioned above in connection with the description of the compounds of the formula (X) according to the invention as being preferred, or particularly preferred, for $R^a$.

Examples of the starting substances of the formula (XI) which may be mentioned are: 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-phenylsulphonyl isocyanate, 2-fluoro-, 2-chloro-, 2-difluoromethoxy-, 2-trifluoromethoxy-, 2-methoxycarbonyl- and 2-ethoxycarbonyl-benzylsulphonyl isocyanate, 2-methoxycarbonyl-3-thienyl-sulphonyl isocyanate, 4-methoxycarbonyl- and 4-ethoxycarbonyl-1-methyl-pyrazol-5-yl-sulphonyl isocyanate.

The sulphonyl isocyanates of the formula (XI) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (a) according to the invention for the preparation of the new compounds of the formula (X) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

When carrying out process (a) according to the invention, the reaction temperatures can be varied within a substantial range. In general, the process is carried out at temperatures between 0° C. and 150° C., preferably at temperatures between 10° C. and 80° C.

In general, process (a) according to the invention is carried out under atmospheric pressure.

For carrying out process (a) according to the invention, between 1 and 3 moles, preferably between 1 and 2 moles, of sulphonyl isocyanate of the formula (XI) are generally employed per mole or triazolinone of the formula (II).

The reactants can be combined in any desired sequence. The reaction mixture is stirred until the reaction is complete and the product is isolated by filtration with suction. In another processing variant, the mixture is concentrated, and the crude product which remains in the residue is brought to crystallisation with a suitable solvent such as, for example, diethyl ether. The product of the formula (X) which is obtained in this way in crystalline form is isolated by filtration with suction.

Formula (XII) provides a general definition of the triazolinone derivatives to be used as starting substances in process (b) according to the invention for the preparation of compounds of the formula (X).

In formula (XII), $R^2$ and $R^3$ preferably, or in particular, have those meanings which have already been mentioned above in connection with description of the compounds of the formula (X) according to the invention as being preferred, or particularly preferred, for $R^2$ and $R^3$ and $Z^1$ preferably represents chlorine, $C_1$–$C_4$-alkoxy, benzyloxy or phenoxy, in particular methoxy or phenoxy.

Examples of the starting substances of the formula (XII) which are possible are the compounds of the formula (XII) which are to be prepared from the compounds of the formula (II) listed in Table 3 and phosgene, methyl chloroformate, benzyl chloroformate, phenyl chloroformate or diphenyl carbonate.

The starting substances of the formula XII were hitherto unknown.

The new triazolinone derivatives of the formula XII are obtained when triazolinones of the general formula (II)

in which $R^2$ and $R^3$ have the abovementioned meanings are reacted with carbonic acid derivatives of the general formula (XVIII)

$$Z^1\text{—CO—}Z^2 \qquad (XVIII)$$

in which $Z^1$ has the abovementioned meaning and $Z^2$ represents a leaving group such as chlorine, methoxy, benzyloxy or phenoxy, if appropriate in the presence of a diluent such as, for example, tetrahydrofuran, and, if appropriate, in the presence of an acid acceptor such as, for example, sodium hydride or potassium tert-butylate, at temperatures between −20° C. and +100° C.

Formula (XVIII) provides a general definition of the sulphonamides furthermore to be used as starting substances in process (b) according to the invention for the preparation of compounds of the formula (X).

In formula (XIII), $R^a$ preferably, or in particular, has that meaning which has already been mentioned above in connection with the description of the compounds of the formula (X) according to the invention as being preferred, or particularly preferred, for $R^a$.

The following may be mentioned as examples of the starting substances of the formula (XIII): 2-fluoro-, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulphinyl-, 2-methylsulphonyl-, 2-dimethylaminosulphonyl-, 2-diethylaminosulphonyl-, 2-(N-methoxy-N-methyl)-aminosulphonyl-, 2-phenyl-, 2-phenoxy-, 2-methoxycarbonyl-, 2-ethoxycarbonyl-, 2-propoxycarbonyl- and 2-isopropoxycarbonyl-benzenesulphonamide, 2-fluoro-, 2-Chloro-, 2-difluoromethoxy-, 2-trifluoromethoxy-, 2-methoxycarbonyl- and 2-ethoxycarbonyl-phenylmethanesulphonamide, 2-methoxycarbonyl-3-thiophenesulphonamide, 4-methoxycarbonyl- and 4-ethoxycarbonyl-1-methyl-pyrazole-5-sulphonamide.

The sulphonamides of the formula (XIII) are known and/or can be prepared by processes known per se (cf. U.S. Pat. Nos. 4,127,405, 4,169,719, 4,371,391; EP-A 7,687, 13,480, 21,641, 23,141, 23,422, 30,139, 35,893, 44,808, 44,809, 48,143, 51,466, 64,322, 70,041, 173,312).

Process (b) according to the invention for the preparation of the new compounds of the formula (X) is preferably carried out using diluents. Diluents which are suitable for this purpose are virtually all inert organic solvents as have been indicated, for example, above in the case of process (a) according to the invention.

Acid acceptors which can be employed in process (b) according to the invention are all acid-binding agents which can customarily be employed for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4.3.0]-non-5-ene (DBN), 1,8-diazabicyclo-[5.4.0]-undec-7-ene (DBU) and 1,4-diazabicyclo[2.2.2]-octane (DABCO).

When carrying out process (b) according to the invention, the reaction temperatures can be varied within a substantial range. In general, the process is carried out at temperatures between 0° C. and 100° C., preferably at temperatures between 10° C. and 60° C.

Process (b) according to the invention is generally carried out under atmospheric pressure. However, it can also be carried out under increased or reduced pressure.

For carrying out process (b) according to the invention, the starting substances required in each case are generally employed in approximately equimolar amounts. However, it is also possible to use one of the two components employed in each case in a larger excess. In general, the reactions are carried out in a suitable diluent in the presence of an acid acceptor, and the reaction mixture is stirred for several hours at the particular temperature required. Working-up in process (b) according to the invention is carried out in each case by customary methods.

The triazolinones of the formula (II) to be used as starting substances in process (c) according to the invention for the preparation of compounds of the formula (X) have already been described as starting substances for process (a) according to the invention.

Formula (XIV) provides a general definition of the sulphonamide derivatives furthermore to be used as starting substances in process (c) according to the invention for the preparation of compounds of the formula (X).

In formula (XIV), $R^a$ and $Z^1$ preferably, or in particular, have those meanings which have already been mentioned above in connection with the description of the compounds of the formula (X) or (XII) according to the invention as being preferred, or particularly preferred, for $R^a$ and $Z^1$.

Process (c) according to the invention is preferably carried out using diluents. Solvents which are suitable for this purpose are the same organic solvents as have been mentioned above in connection with the description of process (a) according to the invention.

If appropriate, process (c) is carried out in the presence of an acid acceptor. Acid-binding agents which are suitable for this purpose are the same as have been mentioned above in connection with the description of process (b) according to the invention.

When carrying out process (c), the reaction temperatures can vary within a substantial range. In general, the process is carried out at temperatures between 0° C. and 100° C., preferably at temperatures between 10° C. and 60° C.

In general, process (c) according to the invention is carried out under atmospheric pressure. However, the process can also be carried out under increased or reduced pressure.

For carrying out process (c) according to the invention, the starting substances required in each case are generally employed in approximately equimolar amounts. However, it is also possible to use one of the two components employed in each case in a larger excess. The reactions are generally carried out in a suitable diluent in the presence of an acid acceptor, and the reaction mixture is stirred for several hours at the particular temperature required. Working-up is carried out in process (c) according to the invention in each case by customary methods.

To convert the compounds of the formula (X) into salts, they are stirred with suitable salt formers such as, for example, sodium hydroxide, sodium methylate, sodium ethylate, potassium hydroxide, potassium methylate or potassium ethylate, ammonia, isopropylamine, dibutylamine or triethylamine, in suitable diluents such as, for example, water, methanol or ethanol. The salts can be isolated in the form of crystalline products, if appropriate after concentration.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The compounds of the formula (I) according to the invention are suitable for selectively combating monocotyledon and dicotyledon weeds, mainly in monocotyledon cultures, by the pre- and the post-emergence method.

Some of the compounds of the formula (X) according to the invention are suitable for total or semi-total weed control, some for the selective control of monocotyledon and dicotyledon weeds in monocotyledon and dicotyledon cultures, both pre-emergence and post-emergence.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-(4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-2', 6'-diethyl-N-methoxy-methylacetanilide (ALACHLOR); methyl-6,6-dimethyl-2,4-dioxo-3-[1-(2-propenyloxyamino)-butylidene]-cyclohexanecarboxylic acid (ALLOXYDIM); 4-aminobenzenesulphonyl methyl carbamate (ASULAM); 2-chloro-4-ethylamino-6-isopropylamino-1,3,5-triazine (ATRAZINE); methyl 2-[[[[(4,6-dimethoxypyrimidin-2-yl)-amino]carbonyl]-amino]-sulphonyl]-methyl]-benzoate (BENSULFURON); 3-isopropyl-2,1,3-benzothiadiazin-4-one-2,2-dioxide (BENTAZONE); 3,5-dibromo-4-hydroxy-benzonitrile (BROMOXYNIL); N-(butoxymethyl)-2-chloro-N-(2,6-diethylphenyl)-acetamide (BUTACHLOR); 5-amino-4-chloro-2-phenyl-2,3-dihydro-3-oxy-pyridazine (CHLORIDAZONE); isopropyl N-(3-chlorophenyl)-carbamate (CHLORPROPHAM); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methyl-phenyl)-urea (CHLORTOLURON); exo-1-methyl-4-(1-methyl-ethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexyl-thiolcarbamate (CYCLOATE); 2-[1-(ethoximino)-butyl]-3-hydroxy-5-[tetrahydro-(2H)-thiopyran- 3-yl]-2-cyclohexene-1-one (CYCLOXYDIM); 2-[4-(2,4-dichlorophenoxy)-phenoxy]-propionic acid, its methyl ester or its ethyl ester (DICLOFOP); 2-[(2-chlorophenyl)methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro-2-benzoxazolyl)-oxy]phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)carbonyl]-amino]-sulphonyl}-benzoic acid or its methyl ester (METSULFURON); S-ethyl N,N-hexamethylene-thiocarbamate (MOLINATE); 1-(3-trifluoromethylphenyl)-4-methylamino-5-chloro-6-pyridazone (NORFLURAZON); 4-(di-n-propyl-amino)-3,5-dinitrobenzenesulphonamide (ORYZALIN); N-(1-ethylpropyl)-3,4-dimethyl-2,6-dinitroaniline (PENDIMETHALIN); 3-(ethoxycarbonylaminophenyl)-N-(3'-methylphenyl)-carbamate (PHENMEDIPHAM); 2-chloro-N-isopropylacetanilide (PROPACHLOR); isopropyl N-phenyl-carbamate (PROPHAM); O-(6-chloro-3-phenyl-pyridazin-4-yl) S-octyl thiocarbonate (PYRIDATE); ethyl 2-[4-(6-chloroquinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chlorophenyl)-methyl]N,N-diethylthiocarbamate (THIOBENCARB); S-(2,3,3-trichloroallyl) N,N-diisopropylthiocarbamate (TRIALLATE); 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 10 g and 5 kg per ha.

The preparation and use of the active compounds according to the invention can be seen from the following examples.

PREPARATION EXAMPLES

Example 1

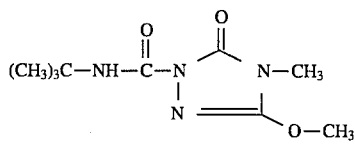

A mixture of 1.3 g (0.01 mol) of 5-methoxy-4-methyl-2,4-dihydro-3H-1,2,4-triazol-3-one, 0.1 g of 1,8-diazabicyclo[5.4.0]undec-7-ene (DBU), 1.0 g (0.01 mol) of tertbutyl isocyanate and 50 ml of acetonitrile is stirred for 12 hours at 20° C. and subsequently concentrated under a water pump vacuum. The residue is taken up in methylene chloride, and the mixture is washed with water, dried with magnesium sulphate and filtered. The filtrate is concentrated under a water pump vacuum, the residue is brought to crystallisation by trituration with petroleum ether, and the product is isolated by filtration with suction.

1.4 g (61% Of theory) of 2-tert-butyl-amino-carbonyl-5-methoxy-4-methyl-2,4-dihydro-3H-1,2,4-triazol-3-one of melting point 167° C. are obtained.

Other examples of the compounds of the formula (I) which can be prepared analogously to Example 1 and corresponding to the general description of the preparation processes according to the invention are those listed in Table 4 below.

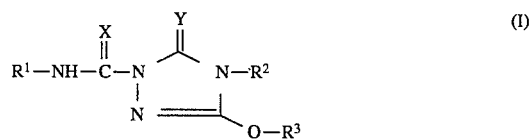

TABLE 4

| | Preparation examples of the compounds of the formula (I) | | | | | |
|---|---|---|---|---|---|---|
| Example No. | R¹ | R² | R³ | X | Y | Melting point (°C.) |
| 2 | CH₃<br>\|<br>ClCH₂C—<br>\|<br>CH₃ | CH₃ | CH₃ | O | O | 153 |
| 3 | H₃CO—⟨phenyl⟩—OCH₂CH—<br>\|<br>CH₃ | C₃H₇ | CH₃ | O | O | (oil) |

TABLE 4-continued

Preparation examples of the compounds of the formula (I)

| Example No. | R¹ | R² | R³ | X | Y | Melting point (°C.) |
|---|---|---|---|---|---|---|
| 4 | 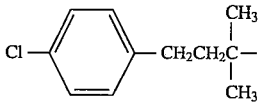 4-Cl-C₆H₄-CH₂CH₂C(CH₃)₂- | C₃H₇ | CH₃ | O | O | (oil) |
| 5 | 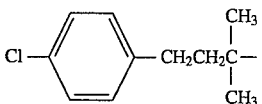 4-Cl-C₆H₄-CH₂CH₂C(CH₃)₂- | CH₃ | C₂H₅ | O | O | (oil) |
| 6 | 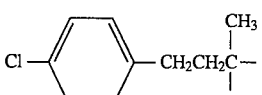 4-Cl-C₆H₄-CH₂CH₂CH(CH₃)- | C₂H₅ | CH₃ | O | O | (oil) |
| 7 | 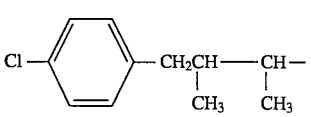 4-Cl-C₆H₄-CH₂CH(CH₃)CH(CH₃)- | CH₃ | C₂H₅ | O | O | (oil) |
| 8 | 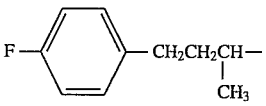 4-F-C₆H₄-CH₂CH₂CH(CH₃)- | CH₃ | C₂H₅ | O | O | (oil) |
| 9 | 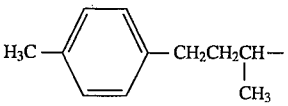 4-CH₃-C₆H₄-CH₂CH₂CH(CH₃)- | CH₃ | C₂H₅ | O | O | (oil) |
| 10 | 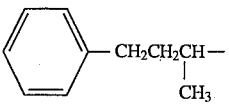 C₆H₅-CH₂CH₂CH(CH₃)- | CH₃ | C₂H₅ | O | O | (oil) |
| 11 | 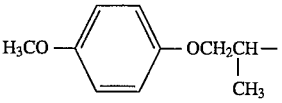 4-CH₃O-C₆H₄-OCH₂CH(CH₃)- | CH₃ | C₂H₅ | O | O | (oil) |
| 12 | 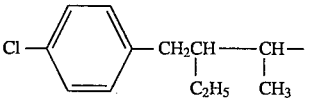 4-Cl-C₆H₄-CH₂CH(C₂H₅)CH(CH₃)- | CH₃ | C₂H₅ | O | O | (oil) |
| 13 | 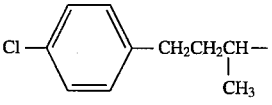 4-Cl-C₆H₄-CH₂CH₂CH(CH₃)- | CH₃ | C₂H₅ | O | O | (oil) |
| 14 | 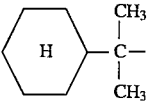 cyclohexyl-C(CH₃)₂- | CH₃ | CH₃ | O | O | 166 |
| 15 | 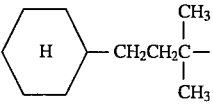 cyclohexyl-CH₂CH₂C(CH₃)₂- | CH₃ | CH₃ | O | O | 120 |
| 16 | 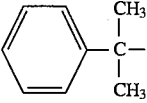 C₆H₅-C(CH₃)₂- | CH₃ | CH₃ | O | O | 176 |

TABLE 4-continued

Preparation examples of the compounds of the formula (I)

| Example No. | R¹ | R² | R³ | X | Y | Melting point (°C.) |
|---|---|---|---|---|---|---|
| 17 | 4-Cl-C$_6$H$_4$-C(CH$_3$)(CH$_3$)-CH$_2$CH$_2$- | CH$_3$ | CH$_3$ | O | O | 130 |
| 18 | 2,4-Cl$_2$-C$_6$H$_3$-CH(CH$_3$)- | CH$_3$ | CH$_3$ | O | O | 104 |
| 19 | C$_6$H$_5$-CH$_2$CH$_2$-C(CH$_3$)(CH$_3$)- | CH$_3$ | CH$_3$ | O | O | 117 |
| 20 | 4-CH$_3$-C$_6$H$_4$-CH(CH$_3$)- | CH$_3$ | CH$_3$ | O | O | 100 |
| 21 | (CH$_3$)$_3$C- | CH$_3$ | C$_3$H$_7$ | O | O | 75 |
| 22 | ClCH$_2$-C(CH$_3$)(CH$_3$)- | CH$_3$ | C$_3$H$_7$ | O | O | 95 |
| 23 | C$_6$H$_5$-CH$_2$-C(CH$_3$)(CH$_3$)- | CH$_3$ | CH$_3$ | O | O | 142 |
| 24 | H$_9$C$_4$-C(CH$_3$)(CH$_3$)- | CH$_3$ | CH$_3$ | O | O | 135 |
| 25 | 4-H$_3$CO-C$_6$H$_4$-CH$_2$CH$_2$-C(CH$_3$)(CH$_3$)- | CH$_3$ | CH$_3$ | O | O | 106 |
| 26 | C$_6$H$_5$-CH$_2$CH$_2$CH$_2$-C(CH$_3$)(CH$_3$)- | CH$_3$ | CH$_3$ | O | O | 137 |
| 27 | C$_6$H$_{11}$-CH$_2$-C(CH$_3$)(CH$_3$)- | CH$_3$ | CH$_3$ | O | O | 131 |
| 28 | 4-Cl-C$_6$H$_4$-CH$_2$CH$_2$-C(CH$_3$)(CH$_3$)- | CH$_3$ | CH$_3$ | O | O | 118 |
| 29 | 4-F$_2$CHO-C$_6$H$_4$-C≡C-C(CH$_3$)(CH$_3$)- | CH$_3$ | CH$_3$ | O | O | 82 |
| 30 | (CH$_3$)$_3$C- | CH$_2$-CH=CH$_2$ | CH$_3$ | O | O | 87 |
| 31 | (CH$_3$)$_3$C- | n-C$_3$H$_7$ | CH$_3$ | O | O | 144 |
| 32 | (CH$_3$)$_3$C- | CH$_3$ | C$_2$H$_5$ | O | O | 102–103 |
| 33 | (CH$_3$)$_3$C- | CH$_3$ | C$_4$H$_9$-n | O | O | 79–80 |

TABLE 4-continued

Preparation examples of the compounds of the formula (I)

| Example No. | R¹ | R² | R³ | X | Y | Melting point (°C.) |
|---|---|---|---|---|---|---|
| 34 | (CH₃)₃C— |  | C₂H₅ | O | O | 108 |
| 35 | (CH₃)₃C— | C₂H₅ | CH₃ | O | O | 144–146 |
| 36 | (CH₃)₃C— | CH₂—CH=CH₂ | C₂H₅ | O | O | 63–64 |
| 37 | (CH₃)₃C— | i-C₃H₇ | C₂H₅ | O | O | 68–69 |
| 38 | (CH₃)₃C— | (CH₂)₃—OCH₃ | CH₃ | O | O | 86–87 |
| 39 | (CH₃)₃C— | n-C₃H₇ | C₂H₅ | O | O | 70–71 |
| 40 | 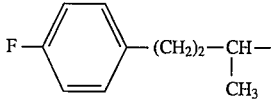 | CH₃ | C₄H₉-n | O | O | Oil |
| 41 | 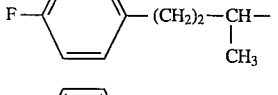 |  | C₂H₅ | O | O | Oil |
| 42 | 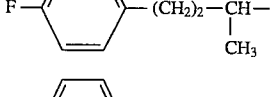 | C₂H₅ | CH₃ | O | O | Oil |
| 43 | 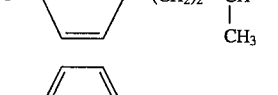 | CH₃ | i-C₃H₇ | O | O | Oil |
| 44 | 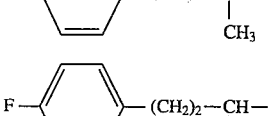 | n-C₃H₇ | CH₃ | O | O | 78 |
| 45 | 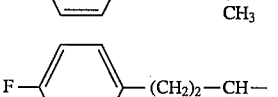 | CH₂—CH=CH₂ | C₂H₅ | O | O | Oil |
| 46 | 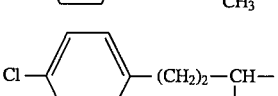 | n-C₃H₇ | CH₃ | O | O | 93–94 |
| 47 | 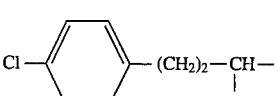 | CH₃ | C₄H₉-n | O | O | Oil |
| 48 | 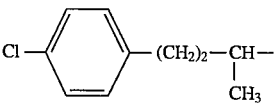 |  | C₂H₅ | O | O | Oil |
| 49 | 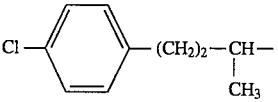 | C₂H₅ | CH₃ | O | O | Oil |
| 50 | 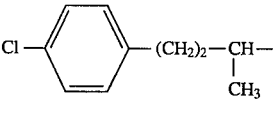 | CH₂—CH=CH₂ | C₂H₅ | O | O | Oil |
| 51 |  | i-C₃H₇ | C₂H₅ | O | O | Oil |

TABLE 4-continued

Preparation examples of the compounds of the formula (I)

| Example No. | R¹ | R² | R³ | X | Y | Melting point (°C.) |
|---|---|---|---|---|---|---|
| 52 | Cl—C₆H₄—(CH₂)₂—CH(CH₃)— | (CH₂)₃—OCH₃ | CH₃ | O | O | 104–105 |
| 53 | Cl—C₆H₄—(CH₂)₂—CH(CH₃)— | n-C₃H₇ | C₂H₅ | O | O | Oil |
| 54 | Cl—C₆H₄—(CH₂)₂—CH(CH₃)— | i-C₃H₇ | CH₃ | O | O | Oil |
| 55 | Cl—C₆H₄—(CH₂)₂—CH(CH₃)— | CH₃ | i-C₃H₇ | O | O | Oil |
| 56 | CH₃—C₆H₄—(CH₂)₂—C(CH₃)₂— | n-C₃H₇ | CH₃ | O | O | Oil |
| 57 | CH₃—C₆H₄—(CH₂)₂—C(CH₃)₂— | CH₃ | C₂H₅ | O | O | Oil |
| 58 | CH₃—C₆H₄—(CH₂)₂—C(CH₃)₂— | C₂H₅ | CH₃ | O | O | Oil |
| 59 | CH₃—C₆H₄—(CH₂)₂—C(CH₃)₂— | CH₂—CH=CH₂ | C₂H₅ | O | O | Oil |
| 60 | CH₃—C₆H₄—(CH₂)₂—C(CH₃)₂— | n-C₃H₇ | C₂H₅ | O | O | Oil |
| 61 | CH₃—C₆H₄—(CH₂)₂—C(CH₃)₂— | i-C₃H₇ | CH₃ | O | O | Oil |
| 62 | CH₃—C₆H₄—(CH₂)₂—C(CH₃)₂— | CH₃ | i-C₃H₇ | O | O | Oil |
| 63 | CF₃—C₆H₄—(CH₂)₂—C(CH₃)₂— | n-C₃H₇ | CH₃ | O | O | Oil |
| 64 | CF₃—C₆H₄—(CH₂)₂—C(CH₃)₂— | CH₃ | C₂H₅ | O | O | Oil |
| 65 | CF₃—C₆H₄—(CH₂)₂—C(CH₃)₂— | CH₃ | n-C₄H₉ | O | O | Oil |

TABLE 4-continued

Preparation examples of the compounds of the formula (I)

| Example No. | R¹ | R² | R³ | X | Y | Melting point (°C.) |
|---|---|---|---|---|---|---|
| 66 | CF₃—C₆H₄—(CH₂)₂—C(CH₃)₂— | C₂H₅ | CH₃ | O | O | Oil |
| 67 | CF₃—C₆H₄—(CH₂)₂—C(CH₃)₂— | n-C₃H₇ | C₂H₅ | O | O | Oil |
| 68 | CF₃—C₆H₄—(CH₂)₂—C(CH₃)₂— | i-C₃H₇ | CH₃ | O | O | Oil |
| 69 | F—C₆H₄—(CH₂)₂—C(CH₃)₂— | n-C₃H₇ | CH₃ | O | O | Oil |
| 70 | F—C₆H₄—(CH₂)₂—C(CH₃)₂— | CH₃ | C₂H₅ | O | O | Oil |
| 71 | F—C₆H₄—(CH₂)₂—C(CH₃)₂— | CH₃ | n-C₄H₉ | O | O | Oil |
| 72 | F—C₆H₄—(CH₂)₂—C(CH₃)₂— | C₂H₅ | CH₃ | O | O | Oil |
| 73 | F—C₆H₄—(CH₂)₂—C(CH₃)₂— | n-C₃H₇ | C₂H₅ | O | O | Oil |
| 74 | 3-CF₃-4-CH₃-C₆H₃—(CH₂)₂—C(CH₃)₂— | n-C₃H₇ | CH₃ | O | O | Oil |
| 75 | 3-CF₃-4-CH₃-C₆H₃—(CH₂)₂—C(CH₃)₂— | CH₃ | C₂H₅ | O | O | Oil |
| 76 | 3-CF₃-4-CH₃-C₆H₃—(CH₂)₂—C(CH₃)₂— | C₂H₅ | CH₃ | O | O | Oil |
| 77 | 3-CF₃-4-CH₃-C₆H₃—(CH₂)₂—C(CH₃)₂— | CH₂—CH=CH₂ | C₂H₅ | O | O | Oil |

TABLE 4-continued

Preparation examples of the compounds of the formula (I)

| Example No. | R¹ | R² | R³ | X | Y | Melting point (°C.) |
|---|---|---|---|---|---|---|
| 78 | 4-CF₃, 3-CH₃-C₆H₃-(CH₂)₂-C(CH₃)₂- | n-C₃H₇ | C₂H₅ | O | O | Oil |
| 79 | 3-Cl-C₆H₄-(CH₂)₂-C(CH₃)₂- | n-C₃H₇ | CH₃ | O | O | 107–108 |
| 80 | 3-Cl-C₆H₄-(CH₂)₂-C(CH₃)₂- | CH₃ | C₄H₉-n | O | O | Oil |
| 81 | 3-Cl-C₆H₄-(CH₂)₂-C(CH₃)₂- | C₂H₅ | CH₃ | O | O | 83–85 |
| 82 | 3-Cl-C₆H₄-(CH₂)₂-C(CH₃)₂- | n-C₃H₇ | C₂H₅ | O | O | 125–127 |
| 83 | 3-Cl-C₆H₄-(CH₂)₂-C(CH₃)₂- | i-C₃H₇ | CH₃ | O | O | 108–110 |
| 84 | 4-Cl-C₆H₄-C(CH₃)₂-CH₂-CH(CH₃)- | n-C₃H₇ | CH₃ | O | O | 100–102 |
| 85 | 2-COOCH₃-C₆H₄- | CH₃ | C₂H₅ | O | O | 164–166 |
| 86 | 2-COOCH₃-C₆H₄- | CH₃ | n-C₄H₉ | O | O | 145 |
| 87 | 2-COOCH₃-C₆H₄- | n-C₃H₇ | CH₃ | O | O | 109–110 |

TABLE 4-continued

Preparation examples of the compounds of the formula (I)

| Example No. | R¹ | R² | R³ | X | Y | Melting point (°C.) |
|---|---|---|---|---|---|---|
| 88 | 2-(COOCH$_3$)-C$_6$H$_4$- | cyclopropyl | C$_2$H$_5$ | O | O | 123–125 |
| 89 | 2-(COOCH$_3$)-C$_6$H$_4$- | n-C$_3$H$_7$ | C$_2$H$_5$ | O | O | 95–98 |
| 90 | 4-Cl-C$_6$H$_4$-C(CH$_3$)$_2$-CH$_2$-CH(CH$_3$)- | CH$_3$ | C$_2$H$_5$ | O | O | 90–91 |
| 91 | 2-Cl-C$_6$H$_4$-(CH$_2$)$_2$-C(CH$_3$)$_2$- | CH$_3$ | C$_2$H$_5$ | O | O | 64–66 |
| 92 | 4-Cl-C$_6$H$_4$-(CH$_2$)-C(C$_2$H$_5$)$_2$- | CH$_3$ | C$_2$H$_5$ | O | O | 84–85 |
| 93 | C$_6$H$_5$-(CH$_2$)-C(C$_2$H$_5$)$_2$- | CH$_3$ | C$_2$H$_5$ | O | O | 104–105 |
| 94 | 2,6-Cl$_2$-C$_6$H$_3$-(CH$_2$)$_2$-C(CH$_3$)$_2$- | CH$_3$ | C$_2$H$_5$ | O | O | 113–116 |
| 95 | 2-thienyl-C≡C-C(CH$_3$)$_2$- | cyclopropyl | C$_2$H$_5$ | O | O | 95 |
| 96 | 3-CN-C$_6$H$_4$-(CH$_2$)$_2$-C(CH$_3$)$_2$- | CH$_3$ | C$_2$H$_5$ | O | O | 115–116 |
| 97 | (CH$_3$)$_3$C- | CH$_3$ | i-C$_3$H$_7$ | O | O | 82–84 |
| 98 | Cl-CH$_2$-C(CH$_3$)$_2$- | n-C$_3$H$_7$ | CH$_3$ | O | O | 93–95 |
| 99 | Cl-CH$_2$-C(CH$_3$)$_2$- | CH$_3$ | n-C$_4$H$_9$ | O | O | 85–87 |
| 100 | Cl-CH$_2$-C(CH$_3$)$_2$- | C$_2$H$_5$ | CH$_3$ | O | O | 127–129 |
| 101 | Cl-CH$_2$-C(CH$_3$)$_2$- | CH$_2$-CH=CH$_2$ | C$_2$H$_5$ | O | O | Oil |
| 102 | Cl-CH$_2$-C(CH$_3$)$_2$- | n-C$_3$H$_7$ | C$_2$H$_5$ | O | O | 63–65 |
| 103 | Cl-CH$_2$-C(CH$_3$)$_2$- | CH$_3$ | i-C$_3$H$_7$ | O | O | 85–87 |
| 104 | Cl-CH$_2$-C(CH$_3$)$_2$- | CH$_3$ | C$_2$H$_5$ | O | O | 95–96 |
| 105 | 2-(COOCH$_3$)-C$_6$H$_4$- | CH$_3$ | i-C$_3$H$_7$ | O | O | 146 |

TABLE 4-continued

Preparation examples of the compounds of the formula (I)

| Example No. | R¹ | R² | R³ | X | Y | Melting point (°C.) |
|---|---|---|---|---|---|---|
| 106 | Cl—C₆H₄—CH₂—CH(C₂H₅)—CH(CH₃)— | CH₃ | i-C₃H₇ | O | O | Oil |
| 107 | (2-Cl-C₆H₄)—(CH₂)₂—CH(CH₃)— | CH₃ | i-C₃H₇ | O | O | Oil |
| 108 | F—C₆H₄—O—CH₂—C(CH₃)₂—CH(CH₃)— | CH₃ | i-C₃H₇ | O | O | Oil |
| 109 | F—C₆H₄—O—CH₂—C(CH₃)₂—CH(CH₃)— | CH₃ | C₂H₅ | O | O | 115–117 |
| 110 | F—C₆H₄—O—CH₂—C(CH₃)₂—CH(CH₃)— | C₂H₅ | CH₃ | O | O | 129–130 |
| 111 | F—C₆H₄—O—CH₂—C(CH₃)₂—CH(CH₃)— | cyclopropyl | C₂H₅ | O | O | Oil |
| 112 | (CH₃)₃C— | CH₃ | (CH₂)₂—OC₂H₅ | O | O | 58 |
| 113 | Cl—CH₂—C(CH₃)₂— | CH₃ | (CH₂)₂—OC₂H₅ | O | O | Oil |
| 114 | (2-COOCH₃-C₆H₄)— | CH₃ | (CH₂)₂—OC₂H₅ | O | O | 126–128 |
| 115 | F—C₆H₄—(CH₂)₂—CH(CH₃)— | CH₃ | (CH₂)₂—OC₂H₅ | O | O | Oil |
| 116 | F—C₆H₄—(CH₂)₂—CH(CH₃)— | CH₃ | (CH₂)₂—OCH₃ | O | O | Oil |
| 117 | Cl—C₆H₄—O—CH₂—CH(CH₃)— | CH₃ | (CH₂)₂—OCH₃ | O | O | Oil |
| 118 | n-C₆H₁₃—CH(CH₃)— | CH₃ | CH₃ | O | O | 83 |
| 119 | (CH₃)₃C—CH(CH₃)— | CH₃ | CH₃ | O | O | 169 |
| 120 | cyclohexyl-CH(CH₃)— | CH₃ | CH₃ | O | O | 117 |
| 121 | (CH₃)₂CH—CH₂— | CH₃ | CH₃ | O | O | 120 |

TABLE 4-continued

Preparation examples of the compounds of the formula (I)

| Example No. | R¹ | R² | R³ | X | Y | Melting point (°C.) |
|---|---|---|---|---|---|---|
| 122 | cyclohexyl-H | $CH_3$ | $CH_3$ | O | O | 171 |
| 123 | n-$C_3H_7$—C($CH_3$)$_2$— | $CH_3$ | $CH_3$ | O | O | 147 |
| 124 | cyclopentyl | $CH_3$ | $CH_3$ | O | O | 139 |
| 125 | 1-methylcyclohexyl (H, $CH_3$) | $CH_3$ | $CH_3$ | O | O | 165 |
| 126 | $CH_3$—C($C_2H_5$)$_2$— | $CH_3$ | $CH_3$ | O | O | 149 |
| 127 | NC—$CH_2$—CH($C_2H_5$)— | $CH_3$ | $CH_3$ | O | O | 92 |
| 128 | n-$C_5H_{11}$—CH($CH_3$)— | $CH_3$ | $CH_3$ | O | O | 105 |
| 129 | ($CH_3$)$_3$C—$CH_2$—CH($CH_3$)— | $CH_3$ | $CH_3$ | O | O | 104 |
| 130 | ($CH_3$)$_3$C-cyclohexyl-H | $CH_3$ | $CH_3$ | O | O | 182 |
| 131 | n-$C_4H_9$—CH($C_2H_5$)—$CH_2$— | $CH_3$ | $CH_3$ | O | O | 61 |
| 132 | ($C_2H_5$)$_3$C— | $CH_3$ | $CH_3$ | O | O | 148 |
| 133 | $C_2H_5$—C($CH_3$)$_2$— | $CH_3$ | $CH_3$ | O | O | 151 |
| 134 | $C_2H_5$-cyclohexyl-H | $CH_3$ | $CH_3$ | O | O | 126 |
| 135 | cyclopropyl-CH($CH_3$)— | $CH_3$ | $CH_3$ | O | O | 128 |
| 136 | cycloheptyl | $CH_3$ | $CH_3$ | O | O | 146 |
| 137 | n-$C_6H_{13}$— | $CH_3$ | $CH_3$ | O | O | 110 |
| 138 | ($CH_3$)$_3$C—$CH_2$—C($CH_3$)$_2$— | $CH_3$ | $CH_3$ | O | O | 150 |
| 139 | ($CH_3$)$_2$CH—CH($CH_3$)— | $CH_3$ | $CH_3$ | O | O | 126 |
| 140 | HC≡C—C($CH_3$)$_2$— | $CH_3$ | $CH_3$ | O | O | 198 |
| 141 | 1-ethylcyclohexyl (H, $C_2H_5$) | $CH_3$ | $CH_3$ | O | O | 165 |

TABLE 4-continued

Preparation examples of the compounds of the formula (I)

| Example No. | R¹ | R² | R³ | X | Y | Melting point (°C.) |
|---|---|---|---|---|---|---|
| 142 | cyclopropyl | $CH_3$ | $CH_3$ | O | O | 154 |
| 143 | $(CH_3)_2CH-CH_2-CH_2-$ | $CH_3$ | $CH_3$ | O | O | 135 |
| 144 | $(CH_3)_2CH-C(CH_3)_2-$ | $CH_3$ | $CH_3$ | O | O | 158 |
| 145 | $Cl_2CH-C(CH_3)_2-$ | $CH_3$ | $CH_3$ | O | O | 153 |
| 146 | $(CH_3)_2CH-CH_2-$(cyclohexyl-H)$-$ | $CH_3$ | $CH_3$ | O | O | 129 |
| 147 | $n\text{-}C_5H_{11}$ | $CH_3$ | $CH_3$ | O | O | 107 |
| 148 | $(C_2H_5)_2CH-CH_2$ | $CH_3$ | $CH_3$ | O | O | 91 |
| 149 | $C_2H_5-CH(CH_3)-CH(C_2H_5)-CH_2-$ | $CH_3$ | $CH_3$ | O | O | 85 |
| 150 | $(CH_3)_2CH-$ | $CH_3$ | $CH_3$ | O | O | 118 |
| 151 | $(Cl-CH_2)_2C(CH_3)-$ | $CH_3$ | $CH_3$ | O | O | 153 |
| 152 | $F-CH_2-C(CH_3)_2-$ | $CH_3$ | $CH_3$ | O | O | 151 |
| 153 | phenyl-$CH_2-CH(CH_3)-$ | $CH_3$ | $CH_3$ | O | O | 123 |
| 154 | $C_2H_5$-(phenyl)-$CH(CH_3)-$ | $CH_3$ | $CH_3$ | O | O | 91 |
| 155 | $Cl$-(phenyl)-$C(CH_3)_2-CH_2-$ | $CH_3$ | $CH_3$ | O | O | 173 |
| 156 | $CH_3$-(cyclohexyl-H)$-$ | $CH_3$ | $CH_3$ | O | O | 149 |
| 157 | $Cl$-(phenyl)-$CH_2-$ | $CH_3$ | $CH_3$ | O | O | 147 |
| 158 | $n\text{-}C_3H_7-CH(CH_3)-$ | $CH_3$ | $CH_3$ | O | O | 87 |
| 159 | cyclopentyl-($CH_3$) | $CH_3$ | $CH_3$ | O | O | 162 |
| 160 | $(CH_3)_3C-CH_2-CH(CH_3)-CH_2-CH_2-$ | $CH_3$ | $CH_3$ | O | O | 60 |
| 161 | $n\text{-}C_3H_7$ | $CH_3$ | $CH_3$ | O | O | 107 |
| 162 | phenyl-$CH(C_2H_5)-$ | $CH_3$ | $CH_3$ | O | O | 131 |
| 163 | $Cl-CH_2-CH_2-$ | $CH_3$ | $CH_3$ | O | O | 117 |

TABLE 4-continued

Preparation examples of the compounds of the formula (I)

| Example No. | R¹ | R² | R³ | X | Y | Melting point (°C.) |
|---|---|---|---|---|---|---|
| 164 | C₂H₅—CH—<br>　　　\|<br>　　　CH₃ | CH₃ | CH₃ | O | O | 96 |
| 165 | Cl—C₆H₄—CH₂—CH₂—CH(CH₃)— | CH₃ | CH₃ | O | O | 86 |
| 166 | (H₃C)₂C₆H₃—O—CH₂—CH(CH₃)— | CH₃ | CH₃ | O | O | 85 |
| 167 | (CH₃)₂-chromane—O—CH₂—CH(CH₃)— | CH₃ | CH₃ | O | O | 90 |
| 168 | CH₃-cyclohexyl- (H) | CH₃ | CH₃ | O | O | 107 |
| 169 | CH₃—O—CH₂—CH—<br>　　　　　　\|<br>　　　　　　CH₃ | CH₃ | CH₃ | O | O | 94 |
| 170 | F—C₆H₄—O—CH₂—C(CH₃)₂—CH(CH₃)— | CH₃ | CH₃ | O | O | 122 |
| 171 | CH₃-cyclohexyl- (H) | CH₃ | CH₃ | O | O | 137 |
| 172 | CH₃—O—C₆H₄—CH₂—CH₂— | CH₃ | CH₃ | O | O | 139 |
| 173 | CH₃—O—C₆H₄—O—CH₂—CH(CH₃)— | CH₃ | CH₃ | O | O | 91 |
| 174 | C₆H₅—CH₂—CH₂—CH(CH₃)— | CH₃ | CH₃ | O | O | 59 |

PREPARATION EXAMPLES OF COMPOUNDS OF FORMULA X

Example 175

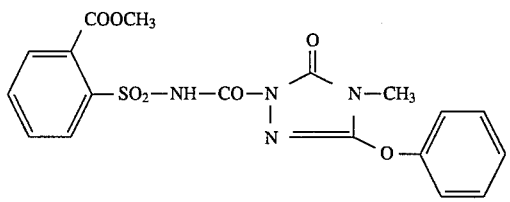

(Process (a))

A mixture of 2.0 g (10.5 mmol) of 4-methyl-5-phenoxy-2,4-dihydro-3H-1,2,4-triazol-3-one, 3.5 g (14.5 mmol) of 2-methoxycarbonyl-phenylsulphonyl isocyanate and 60 ml of acetonitrile is stirred for 6 hours at 20° C. and subsequently concentrated under a water pump vacuum. The residue is stirred with diethyl ether and the product which has precipitated in crystalline form is isolated by filtration with suction.

4.1 g (90% of theory) of 2-(2-methoxycarbonyl-phenyl-sulphonylaminocarbonyl)-4-methyl-5-phenoxy-2,4-dihydro-3H-1,2,4-triazol-3-one of melting point 161° C. are obtained.

Other examples of compounds of the formula (X) which can be prepared analogously to Example 175 and following the general description of the preparation processes according to the invention are those listed in Table 5 below.

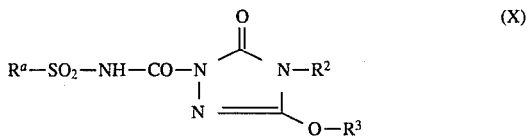

TABLE 5

Preparation Examples of the compounds of the formula (X)

| Example No. | $R^2$ | $R^3$ | $R^a$ | Melting point (°C.) |
|---|---|---|---|---|
| 176 | cyclopropyl | $C_2H_5$ | 2-COOCH$_3$-phenyl | 183 |
| 177 | $CH_3$ | phenyl | 2-CH$_3$-phenyl | 190 |
| 178 | $CH_3$ | $C_3H_7$ | 4-COOC$_2$H$_5$-3-methyl-1-methylpyrazol-5-yl | 120 |
| 179 | $CH_3$ | $C_3H_7$ | 2-F-phenyl | 134 |
| 180 | $CH_3$ | $C_3H_7$ | 2-Br-phenyl | 122 |
| 181 | $CH_3$ | $C_3H_7$ | 2-COOC$_3$H$_7$-phenyl | 125 |

TABLE 5-continued

Preparation Examples of the compounds of the formula (X)

| Example No. | R² | R³ | Rᵃ | Melting point (°C.) |
|---|---|---|---|---|
| 182 | CH₃ | C₂H₅ | 4-COOC₂H₅, 5-CH₃, 1-CH₃-pyrazol-3-yl | 166–167 |
| 183 | CH₃ | C₂H₅ | 2-(COOCH₃)phenyl | 131–132 |
| 184 | CH₃ | C₂H₅ | 2-F-phenyl | 147–148 |
| 185 | CH₃ | C₂H₅ | 2-Br-phenyl | 186–187 |
| 186 | CH₃ | C₂H₅ | 2-(COOC₃H₇)phenyl | 125–126 |
| 187 | CH₃ | C₂H₅ | 2-(COOC₂H₅)phenyl | 123–124 |
| 188 | CH₃ | C₂H₅ | 2-Cl-phenyl | 188–189 |
| 189 | CH₃ | C₂H₅ | 2-Cl-6-CH₃-phenyl | 175–176 |
| 190 | CH₃ | C₂H₅ | 2-OCF₃-phenyl | 152–153 |
| 191 | CH₃ | C₂H₅ | 2-CF₃-phenyl | 172–173 |

TABLE 5-continued

Preparation Examples of the compounds of the formula (X)

| Example No. | $R^2$ | $R^3$ | $R^a$ | Melting point (°C.) |
|---|---|---|---|---|
| 192 | $CH_3$ | $C_2H_5$ | 2-($OCHF_2$)phenyl | 147–148 |
| 193 | $CH_3$ | $C_2H_5$ | 2,6-dichlorobenzyl ($-CH_2-$) | 183–184 |
| 194 | $CH_3$ | $C_2H_5$ | 3-methyl-2-($COOCH_3$)thienyl | 178–183 |
| 195 | $CH_3$ | $C_2H_5$ | 2-($OCF_3$)benzyl ($-CH_2-$) | 155–156 |
| 196 | $CH_3$ | $C_2H_5$ | 2-naphthyl | 162–163 |
| 197 | $CH_3$ | $C_2H_5$ | 2-methylphenyl | 146–147 |
| 198 | $C_3H_7$ | $CH_3$ | 2-($COOCH_3$)phenyl | 129–130 |
| 199 | $C_3H_7$ | $CH_3$ | 2-fluorophenyl | 150–151 |
| 200 | $C_3H_7$ | $CH_3$ | 2-bromophenyl | 130–131 |
| 201 | $C_3H_7$ | $CH_3$ | 2-($COOC_3H_7$)phenyl | 135–136 |

TABLE 5-continued

Preparation Examples of the compounds of the formula (X)

| Example No. | R² | R³ | Rᵃ | Melting point (°C.) |
|---|---|---|---|---|
| 202 | C₃H₇ | CH₃ | 2-(COOC₂H₅)-C₆H₄- | 126–127 |
| 203 | C₃H₇ | CH₃ | 2-Cl-C₆H₄- | 116–117 |
| 204 | C₃H₇ | CH₃ | 4-(COOC₂H₅)-5-methyl-1-methyl-pyrazol-3-yl | 129–130 |
| 205 | C₃H₇ | CH₃ | 2-Cl-6-CH₃-C₆H₃- | 156–157 |
| 206 | C₃H₇ | CH₃ | 2-OCF₃-C₆H₄- | 117–118 |
| 207 | C₃H₇ | CH₃ | 2-CF₃-C₆H₄- | 139–140 |
| 208 | C₃H₇ | CH₃ | 2-OCHF₂-C₆H₄- | 115–116 |
| 209 | C₃H₇ | CH₃ | 2,6-di-Cl-C₆H₃-CH₂- | 183–184 |
| 210 | C₃H₇ | CH₃ | 3-(COOCH₃)-thiophen-2-yl | 130–131 |
| 211 | C₃H₇ | CH₃ | 2-OCF₃-C₆H₄-CH₂- | 108–109 |

TABLE 5-continued
Preparation Examples of the compounds of the formula (X)
| Example No. | $R^2$ | $R^3$ | $R^a$ | Melting point (°C.) |
|---|---|---|---|---|
| 212 | $C_3H_7$ | $CH_3$ | 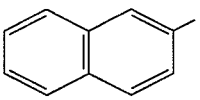 | 122–123 |
| 213 | $C_3H_7$ | $CH_3$ | 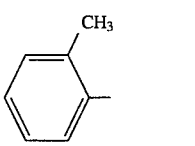 2-CH₃-phenyl | 128–129 |
| 214 | $CH_3$ | $C_4H_9$ | 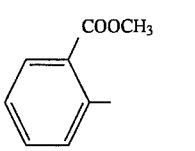 2-COOCH₃-phenyl | 76 |
| 215 | $CH_3$ | $C_4H_9$ | 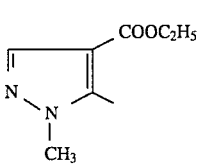 4-COOC₂H₅-3-methyl-1-methylpyrazol-5-yl | 197 |
| 216 | $CH_3$ | $C_4H_9$ | 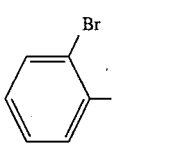 2-Br-phenyl | 153 |
| 217 | $CH_3$ | $C_4H_9$ | 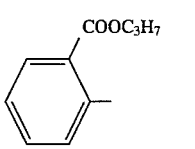 2-COOC₃H₇-phenyl | 105 |
| 218 | $CH_3$ | $C_4H_9$ | 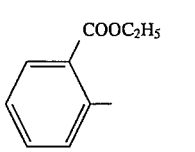 2-COOC₂H₅-phenyl | 81 |
| 219 | $CH_3$ | $C_4H_9$ | 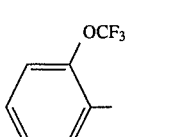 2-OCF₃-phenyl | 137 |
| 220 | $CH_3$ | $C_4H_9$ | 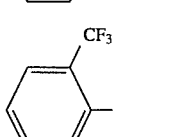 2-CF₃-phenyl | 148 |
| 221 | $CH_3$ | $C_4H_9$ | 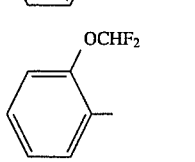 2-OCHF₂-phenyl | 114 |

TABLE 5-continued
Preparation Examples of the compounds of the formula (X)
| Example No. | R² | R³ | Rᵃ | Melting point (°C.) |
|---|---|---|---|---|
| 222 | CH₃ | C₄H₉ | 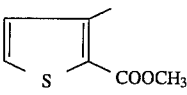 | 147 |
| 223 | CH₃ | C₄H₉ | 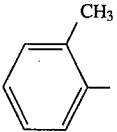 | 139 |
| 224 |  | C₂H₅ | 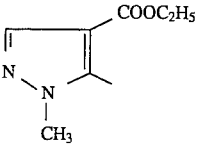 | 114 |
| 225 |  | C₂H₅ | 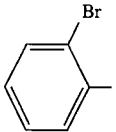 | 135 |
| 226 |  | C₂H₅ | 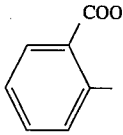 | 108 |
| 227 | CH₃ | 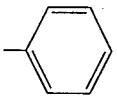 | 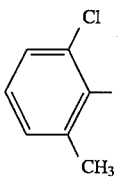 | 209 |
| 228 | CH₃ | 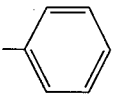 | 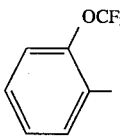 | 191 |
| 229 | CH₃ | 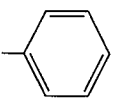 | 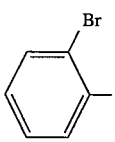 | 207 |
| 230 | CH₃ | CH₃ | 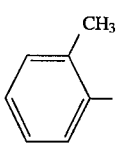 | 154 |
| 231 | CH₃ | CH₃ | 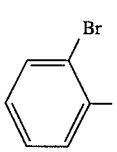 | 187 |

TABLE 5-continued

Preparation Examples of the compounds of the formula (X)

| Example No. | R² | R³ | Rᵃ | Melting point (°C.) |
|---|---|---|---|---|
| 232 | CH₃ | CH₃ | 2-Cl, 3-CH₃-phenyl | 179 |
| 233 | —CH₂—CH═CH₂ | CH₃ | 2-COOCH₃-phenyl | 124 |
| 234 | —CH₂—CH═CH₂ | CH₃ | 2-Cl, 3-CH₃-phenyl | 153 |
| 235 | —CH₂—CH═CH₂ | CH₃ | 2-Br-phenyl | 150 |
| 236 | —CH₂—CH═CH₂ | CH₃ | 2-CH₃-phenyl | 103 |
| 237 | —CH₂—CH═CH₂ | CH₃ | 2-CF₃-phenyl | 130 |
| 238 | CH₃ | CH₃ | 2-CF₃-phenyl | 196 |
| 239 | CH₃ | CH₃ | 2-COOCH₃-phenyl | 136 |
| 240 | —CH₂—CH═CH₂ | CH₃ | 2-COOCH₃-phenyl | 130 |
| 241 | CH₃ | phenyl | 2-CF₃-phenyl | 211 |

TABLE 5-continued
Preparation Examples of the compounds of the formula (X)
| Example No. | R² | R³ | Rᵃ | Melting point (°C.) |
|---|---|---|---|---|
| 242 | CH₃ | 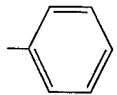 | 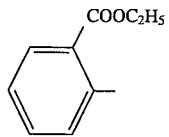 COOC₂H₅ | 179 |
| 243 | CH₃ | CH₃ | 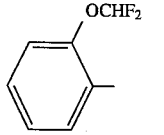 OCHF₂ | 171 |
| 244 | —CH₂—CH═CH₂ | CH₃ | 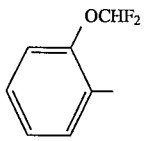 OCHF₂ | 115 |
| 245 | CH₃ | 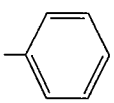 | 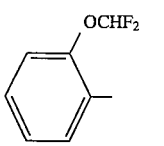 OCHF₂ | 162 |
| 246 | CH₃ | C₃H₇ | 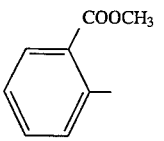 COOCH₃ | 141 |
| 247 | CH₃ | CH₃ | 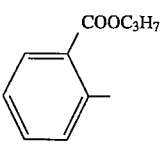 COOC₃H₇ | 148 |
| 248 | CH₃ | 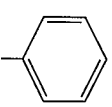 | 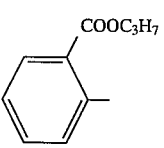 COOC₃H₇ | 174 |
| 249 | —CH₂—CH═CH₂ | CH₃ | 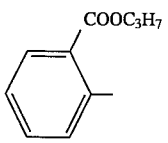 COOC₃H₇ | 138 |
| 250 |  | CH₃ | 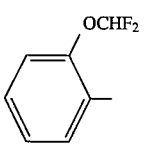 OCHF₂ | 148 |
| 251 |  | CH₃ | 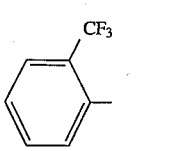 CF₃ | 150 |

TABLE 5-continued

Preparation Examples of the compounds of the formula (X)

| Example No. | R² | R³ | Rᵃ | Melting point (°C.) |
|---|---|---|---|---|
| 252 | —CH₂—CH=CH₂ | CH₃ | 2-OCF₃-phenyl | 125 |
| 253 | CH₃ | CH₃ | 2-OCF₃-phenyl | 145 |
| 254 | C₂H₅ | CH₃ | 2-CO₂CH₃-phenyl | 153–154 |
| 255 | C₂H₅ | CH₃ | 2-F-phenyl | 151–152 |
| 256 | C₂H₅ | CH₃ | 2-Br-phenyl | 167–168 |
| 257 | C₂H₅ | CH₃ | 2-Cl-phenyl | 155–156 |
| 258 | C₂H₅ | CH₃ | 2-Cl-6-CH₃-phenyl | 174–175 |
| 259 | C₂H₅ | CH₃ | 4-CO₂C₂H₅-1-methylpyrazol-5-yl | 140–141 |
| 260 | C₂H₅ | CH₃ | 2-CO₂C₂H₅-phenyl | 160 |
| 261 | C₂H₅ | CH₃ | 2-OCF₃-phenyl | 146–147 |

TABLE 5-continued

Preparation Examples of the compounds of the formula (X)

| Example No. | $R^2$ | $R^3$ | $R^a$ | Melting point (°C.) |
|---|---|---|---|---|
| 262 | $C_2H_5$ | $CH_3$ | 2-($CF_3$)$C_6H_4$— | 156–157 |
| 263 | $C_2H_5$ | $CH_3$ | 2-($OCHF_2$)$C_6H_4$— | 125–126 |
| 264 | $C_2H_5$ | $CH_3$ | 2-($OCF_3$)$C_6H_4$—$CH_2$— | 137–138 |
| 265 | $C_2H_5$ | $CH_3$ | 2,6-$Cl_2$$C_6H_3$—$CH_2$— | 203–204 |
| 266 | $CH_3$ | $C_4H_9$ | 2-F-$C_6H_4$— | 118–119 |
| 267 | $CH_3$ | $C_4H_9$ | 2-Cl-$C_6H_4$— | 146–147 |
| 268 | $CH_3$ | $C_4H_9$ | 2-Cl-6-$CH_3$-$C_6H_3$— | 110–111 |
| 269 | $CH_3$ | $C_4H_9$ | 2-($OCF_3$)$C_6H_4$—$CH_2$— | 123–124 |
| 270 | cyclopropyl | $C_2H_5$ | 2-F-$C_6H_4$— | 152–153 |
| 271 | cyclopropyl | $C_2H_5$ | 2-($CO_2C_2H_5$)$C_6H_4$— | 116–117 |

TABLE 5-continued

Preparation Examples of the compounds of the formula (X)

| Example No. | R² | R³ | Rᵃ | Melting point (°C.) |
|---|---|---|---|---|
| 272 | cyclopropyl | $C_2H_5$ | 2-Cl-phenyl | 145–146 |
| 273 | cyclopropyl | $C_2H_5$ | 2-Cl-3-CH₃-phenyl | 132–133 |
| 274 | cyclopropyl | $C_2H_5$ | 2-OCF₃-phenyl | 88–89 |
| 275 | cyclopropyl | $C_2H_5$ | 2-CF₃-phenyl | 128–129 |
| 276 | cyclopropyl | $C_2H_5$ | 2-OCHF₂-phenyl | 79–77 |
| 277 | —CH₂—CH=CH₂ | $C_2H_5$ | 2-COOCH₃-phenyl | 114–115 |
| 278 | —CH₂—CH=CH₂ | $C_2H_5$ | 4-COOC₂H₅-5-methyl-1-methyl-pyrazol-3-yl | 104–106 |
| 279 | —CH₂—CH=CH₂ | $C_2H_5$ | 2-F-phenyl | 85–86 |
| 280 | —CH₂—CH=CH₂ | $C_2H_5$ | 2-Br-phenyl | 121–122 |
| 281 | —CH₂—CH=CH₂ | $C_2H_5$ | 2-COOC₃H₇-phenyl | 107–108 |

TABLE 5-continued

Preparation Examples of the compounds of the formula (X)

| Example No. | $R^2$ | $R^3$ | $R^a$ | Melting point (°C.) |
|---|---|---|---|---|
| 282 | $-CH_2-CH=CH_2$ | $C_2H_5$ | 2-($COOC_2H_5$)-phenyl | 123–124 |
| 283 | $-CH_2-CH=CH_2$ | $C_2H_5$ | 2-Cl-phenyl | 131–132 |
| 284 | $-CH_2-CH=CH_2$ | $C_2H_5$ | 2-Cl-5-$CH_3$-phenyl | 118–119 |
| 285 | $-CH_2-CH=CH_2$ | $C_2H_5$ | 2-$OCF_3$-phenyl | 110–111 |
| 286 | $-CH_2-CH=CH_2$ | $C_2H_5$ | 2-$CF_3$-phenyl | 123–124 |
| 287 | $-CH_2-CH=CH_2$ | $C_2H_5$ | 2-$OCHF_2$-phenyl | 103–104 |
| 288 | $-CH_2-CH=CH_2$ | $C_2H_5$ | 2,6-di-Cl-phenyl | >250 |
| 289 | $-CH_2-CH=CH_2$ | $C_2H_5$ | 2-$OCF_3$-phenyl-$CH_2-$ | 114–115 |
| 290 | $-CH_2-CH=CH_2$ | $C_2H_5$ | 2-$CH_3$-phenyl | 122–123 |

TABLE 5-continued

Preparation Examples of the compounds of the formula (X)

| Example No. | $R^2$ | $R^3$ | $R^a$ | Melting point (°C.) |
|---|---|---|---|---|
| 291 | $CH(CH_3)_2$ | $C_2H_5$ | 2-($COOCH_3$)phenyl | 188–190 |
| 292 | $CH(CH_3)_2$ | $C_2H_5$ | 4-($COOC_2H_5$)-5-methyl-1-methylpyrazol-3-yl | 230–231 |
| 293 | $CH(CH_3)_2$ | $C_2H_5$ | 2-F-phenyl | 129–130 |
| 294 | $CH(CH_3)_2$ | $C_2H_5$ | 2-Br-phenyl | 207 (Zers.) |
| 295 | $CH(CH_3)_2$ | $C_2H_5$ | 2-($COOC_2H_5$)phenyl | 113–114 |
| 296 | $CH(CH_3)_2$ | $C_2H_5$ | 2-Cl-phenyl | 195–200 |
| 297 | $CH(CH_3)_2$ | $C_2H_5$ | 2-Cl-6-$CH_3$-phenyl | 133–134 |
| 298 | $CH(CH_3)_2$ | $C_2H_5$ | 2-$CF_3$-phenyl | 139–140 |
| 299 | $CH(CH_3)_2$ | $C_2H_5$ | 2-$OCHF_2$-phenyl | 105–106 |
| 300 | $CH(CH_3)_2$ | $C_2H_5$ | 2-$CH_3$-phenyl | 123–124 |

TABLE 5-continued

Preparation Examples of the compounds of the formula (X)

| Example No. | $R^2$ | $R^3$ | $R^a$ | Melting point (°C.) |
|---|---|---|---|---|
| 301 | —(CH$_2$)$_3$—OCH$_3$ | CH$_3$ | 2-(COOCH$_3$)-phenyl | 112–114 |
| 302 | —(CH$_2$)$_3$—OCH$_3$ | CH$_3$ | 4-COOC$_2$H$_5$-5-methyl-2-methyl-pyrazol-3-yl | 92–95 |
| 303 | —(CH$_2$)$_3$—OCH$_3$ | CH$_3$ | 2-F-phenyl | 126–127 |
| 304 | —(CH$_2$)$_3$—OCH$_3$ | CH$_3$ | 2-Br-phenyl | 115–116 |
| 305 | —(CH$_2$)$_3$—OCH$_3$ | CH$_3$ | 2-COOC$_2$H$_5$-phenyl | 112–113 |
| 306 | —(CH$_2$)$_3$—OCH$_3$ | CH$_3$ | 2-OCF$_3$-phenyl | 81–82 |
| 307 | —(CH$_2$)$_3$—OCH$_3$ | CH$_3$ | 2-CF$_3$-phenyl | 104–105 |
| 308 | —(CH$_2$)$_3$—OCH$_3$ | CH$_3$ | 2-OCHF$_2$-phenyl | 113–114 |
| 309 | —(CH$_2$)$_3$—OCH$_3$ | CH$_3$ | 2-CH$_3$-phenyl | 91–92 |
| 310 | n-C$_3$H$_7$ | C$_2$H$_5$ | 2-COOCH$_3$-phenyl | 108 (Zers.) |

TABLE 5-continued

Preparation Examples of the compounds of the formula (X)

| Example No. | R² | R³ | Rᵃ | Melting point (°C.) |
|---|---|---|---|---|
| 311 | n-C₃H₇ | C₂H₅ | 3-methyl-4-(COOC₂H₅)-1-methylpyrazol-5-yl | 212–213 |
| 312 | n-C₃H₇ | C₂H₅ | 2-F-phenyl | 106–107 |
| 313 | n-C₃H₇ | C₂H₅ | 2-Br-phenyl | 127–128 |
| 314 | n-C₃H₇ | C₂H₅ | 2-(COOC₂H₅)-phenyl | 95 (Zers.) |
| 315 | n-C₃H₇ | C₂H₅ | 2-Cl-phenyl | 132–135 |
| 316 | n-C₃H₇ | C₂H₅ | 2-Cl-4-CH₃-phenyl | 138–140 |
| 317 | n-C₃H₇ | C₂H₅ | 2-OCF₃-phenyl | 87–88 |
| 318 | n-C₃H₇ | C₂H₅ | 2-CF₃-phenyl | 108–109 |
| 319 | n-C₃H₇ | C₂H₅ | 2-OCHF₂-phenyl | 154–157 |
| 320 | n-C₃H₇ | C₂H₅ | 2-CH₃-phenyl | 130–133 |

TABLE 5-continued
Preparation Examples of the compounds of the formula (X)
| Example No. | R² | R³ | Rᵃ | Melting point (°C.) |
|---|---|---|---|---|
| 321 | CH(CH₃)₂ | CH₃ | 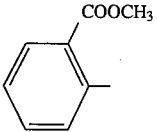 2-COOCH₃-phenyl | 150–151 |
| 322 | CH(CH₃)₂ | CH₃ | 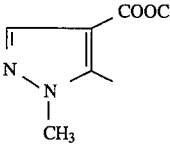 4-COOC₂H₅-5-methyl-1-methylpyrazol-3-yl | 160–161 |
| 323 | CH(CH₃)₂ | CH₃ | 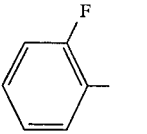 2-F-phenyl | 147–148 |
| 324 | CH(CH₃)₂ | CH₃ | 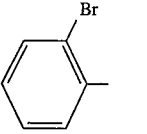 2-Br-phenyl | 148–150 |
| 324 | CH(CH₃)₂ | CH₃ | 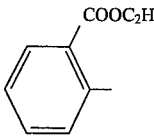 2-COOC₂H₅-phenyl | 143–144 |
| 326 | CH(CH₃)₂ | CH₃ | 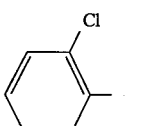 2-Cl-phenyl | 134–135 |
| 327 | CH(CH₃)₂ | CH₃ | 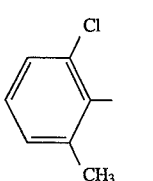 2-Cl-6-CH₃-phenyl | 147–150 |
| 328 | CH(CH₃)₂ | CH₃ | 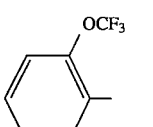 2-OCF₃-phenyl | 148–150 |
| 329 | CH(CH₃)₂ | CH₃ | 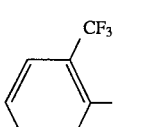 2-CF₃-phenyl | 143–145 |
| 330 | CH(CH₃)₂ | CH₃ | 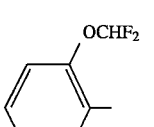 2-OCHF₂-phenyl | 114–116 |

TABLE 5-continued

Preparation Examples of the compounds of the formula (X)

| Example No. | $R^2$ | $R^3$ | $R^a$ | Melting point (°C.) |
|---|---|---|---|---|
| 331 | $CH(CH_3)_2$ | $CH_3$ | 2-$CH_3$-phenyl | 125–128 |
| 332 | $CH_3$ | $CH(CH_3)_2$ | 2-$COOCH_3$-phenyl | 95–97 |
| 333 | $CH_3$ | $CH(CH_3)_2$ | 2-Br-phenyl | 158–160 |
| 334 | $CH_3$ | $CH(CH_3)_2$ | 2-$COOC_2H_5$-phenyl | 152–153 |
| 335 | $CH_3$ | $CH(CH_3)_2$ | 2-$OCF_3$-phenyl | 150–152 |
| 336 | $CH_3$ | $CH(CH_3)_2$ | 2-$CF_3$-phenyl | 128–130 |
| 337 | $CH_3$ | $CH(CH_3)_2$ | 2-$CH_3$-phenyl | 150–152 |
| 338 | $CH_3$ | cyclopentyl | 2-$COOCH_3$-phenyl | 117–118 |
| 339 | $CH_3$ | cyclopentyl | 2-$CH_3$-phenyl | 130–132 |
| 340 | cyclopropyl | $C_2H_5$ | 3-$COOCH_3$-thien-2-yl | 148–150 |
| 341 | $C_2H_5$ | $CH_3$ | 3-$COOCH_3$-thien-2-yl | 172–173 |

TABLE 5-continued

Preparation Examples of the compounds of the formula (X)

| Example No. | $R^2$ | $R^3$ | $R^a$ | Melting point (°C.) |
|---|---|---|---|---|
| 342 | —CH$_2$—CH=CH$_2$ | C$_2$H$_5$ | thiophene-COOCH$_3$ | 130–132 |
| 343 | CH(CH$_3$)$_2$ | C$_2$H$_5$ | thiophene-COOCH$_3$ | 142–144 |
| 344 | —(CH$_2$)$_3$—OCH$_3$ | CH$_3$ | thiophene-COOCH$_3$ | 127–130 |
| 345 | n-C$_3$H$_7$ | C$_2$H$_5$ | thiophene-COOCH$_3$ | 127–130 |
| 346 | CH(CH$_3$)$_2$ | CH$_3$ | thiophene-COOCH$_3$ | 156–157 |
| 347 | CH$_3$ | CH(CH$_3$)$_2$ | thiophene-COOCH$_3$ | 198–200 |
| 348 | CH(CH$_3$)$_2$ | C$_2$H$_5$ | phenyl-COOC$_3$H$_7$-n | 122–124 |
| 349 | —(CH$_2$)$_3$—OCH$_3$ | CH$_3$ | phenyl-COOC$_3$H$_7$-n | 97–98 |
| 350 | n-C$_3$H$_7$ | C$_2$H$_5$ | phenyl-COOC$_3$H$_7$-n | 128–130 |
| 351 | CH(CH$_3$)$_2$ | CH$_3$ | phenyl-COOC$_3$H$_7$-n | 148–150 |
| 352 | CH$_3$ | CH(CH$_3$)$_2$ | phenyl-COOC$_3$H$_7$-n | 154 |
| 353 | C$_2$H$_5$ | CH$_3$ | phenyl-COOC$_3$H$_7$-n | 145 |

TABLE 5-continued

Preparation Examples of the compounds of the formula (X)

| Example No. | R² | R³ | Rª | Melting point (°C.) |
|---|---|---|---|---|
| 354 | CH₃ | C₂H₅ | 2-(OCHF₂)-C₆H₄-CH₂— | 134–136 |
| 355 | CH₃ | C₂H₅ | 2-(SO₂N(CH₃)₂)-C₆H₄— | 178 |
| 356 | CH₃ | n-C₄H₉ | 2-(OCHF₂)-C₆H₄-CH₂— | 142–143 |
| 357 | C₂H₅ | CH₃ | 2-(OCHF₂)-C₆H₄-CH₂— | 115–118 |
| 358 | —CH₂—CH=CH₂ | C₂H₅ | 2-(OCHF₂)-C₆H₄-CH₂— | 98–99 |
| 359 | CH₃ | C₂H₅ | 2-(COOCH₃)-C₆H₄— | 114–115 (Na–Salz) |
| 360 | CH₃ | C₂H₅ | 2-(COOC₃H₇-n)-C₆H₄— | 135–140 (Na–Salz) |
| 361 | CH₃ | CH₃ | 2-(CF₃)-C₆H₄— | 161–163 (Na–Salz) |
| 362 | CH₃ | C₆H₅ | 4-(COOC₂H₅)-1-methyl-pyrazol-5-yl | 185 |
| 363 | CH₃ | C₆H₅ | 3-methyl-2-(COOCH₃)-thien-yl | 202 |

TABLE 5-continued

Preparation Examples of the compounds of the formula (X)

| Example No. | $R^2$ | $R^3$ | $R^a$ | Melting point (°C.) |
|---|---|---|---|---|
| 364 | $CH_3$ | $C_2H_5$ | 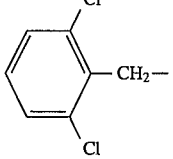 2,6-dichlorobenzyl | 160 (sodium salt) |
| 365 | $CH_3$ | $C_2H_5$ | 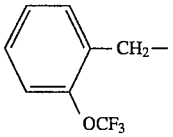 2-(OCF$_3$)benzyl | 144 (sodium salt) |
| 366 | $C_2H_5$ | $CH_3$ | 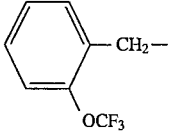 2-(OCF$_3$)benzyl | 180 (sodium salt) |
| 367 | $CH_3$ | $n\text{-}C_4H_9$ | 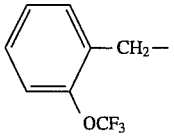 2-(OCF$_3$)benzyl | >270 (sodium salt) |
| 368 | $CH_3$ | $C_2H_5$ | 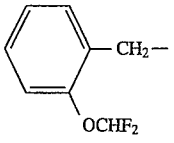 2-(OCHF$_2$)benzyl | 124 (sodium salt) |
| 369 | $CH_3$ | $i\text{-}C_3H_7$ | 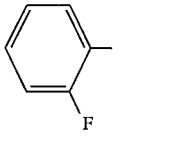 2-fluorophenyl | 160 |
| 370 | $CH_3$ | $i\text{-}C_3H_7$ | 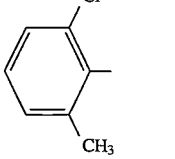 2-chloro-6-methylphenyl | 167 |
| 371 | $CH_3$ | $i\text{-}C_3H_7$ | 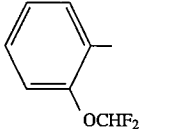 2-(OCHF$_2$)phenyl | 166 |
| 372 | $CH_3$ | $i\text{-}C_3H_7$ | 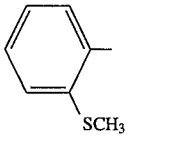 2-(SCH$_3$)phenyl | 145 |
| 373 | $CH_3$ | $i\text{-}C_3H_7$ | 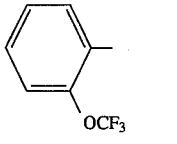 2-(OCF$_3$)phenyl | 126 |

TABLE 5-continued

Preparation Examples of the compounds of the formula (X)

| Example No. | $R^2$ | $R^3$ | $R^a$ | Melting point (°C.) |
|---|---|---|---|---|
| 374 | $CH_3$ | $-C_2H_4OC_2H_5$ | 2-($COOCH_3$)-phenyl | 113 |
| 375 | $CH_3$ | $-C_2H_4OC_2H_5$ | 2-($CH_3$)-phenyl | 102 |
| 376 | $CH_3$ | $-C_2H_4OC_2H_5$ | 2-($COOC_2H_5$)-phenyl | 103 |
| 377 | $CH_3$ | $-C_2H_4OC_2H_5$ | 2-($COOC_3H_7$-n)-phenyl | 114 |
| 378 | $CH_3$ | $-C_2H_4OC_2H_5$ | 2-F-phenyl | 105 |
| 379 | $CH_3$ | $-C_2H_4OC_2H_5$ | 2-($SC_2H_5$)-phenyl | 135 |
| 380 | $CH_3$ | $-C_2H_4OC_2H_5$ | 2-($OCF_3$)-phenyl | 147 |
| 381 | $CH_3$ | $-C_2H_4OC_2H_5$ | 2-Br-phenyl | 127 |
| 382 | $CH_3$ | $-C_2H_4OC_2H_5$ | 2-($SCH_3$)-phenyl | 130 |
| 383 | $CH_3$ | $-C_2H_4OC_2H_5$ | 2-($OCHF_2$)-phenyl | 137 |

TABLE 5-continued

Preparation Examples of the compounds of the formula (X)

| Example No. | R² | R³ | Rᵃ | Melting point (°C.) |
|---|---|---|---|---|
| 384 | CH₃ | —C₂H₄OC₂H₅ | 2-Cl-3-CH₃-phenyl | 127 |
| 385 | CH₃ | —C₂H₄OC₂H₅ | 2-CF₃-phenyl | 155 |
| 386 | CH₃ | —C₂H₄OC₂H₅ | 3-methyl-2-(COOCH₃)-thienyl | 150 |
| 387 | CH₃ | —C₂H₄OCH₃ | 2-(COOC₃H₇-n)-phenyl | 120 |
| 388 | CH₃ | —C₂H₄OCH₃ | 2-SCH₃-phenyl | 109 |
| 389 | CH₃ | —C₂H₄OCH₃ | 2-CH₃-phenyl | 146 |
| 390 | CH₃ | —C₂H₄OCH₃ | 2-Cl-3-CH₃-phenyl | 150 |
| 391 | CH₃ | —C₂H₄OCH₃ | 2-CF₃-phenyl | 170 |
| 392 | CH₃ | —C₂H₄OCH₃ | 3-methyl-2-(COOCH₃)-thienyl | 148 |
| 393 | CH₃ | —C₂H₄OCH₃ | 2-OCF₃-phenyl | 130 |

TABLE 5-continued
Preparation Examples of the compounds of the formula (X)
| Example No. | R² | R³ | Rᵃ | Melting point (°C.) |
|---|---|---|---|---|
| 394 | CH₃ | —C₂H₄OCH₃ | 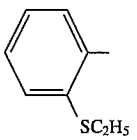 2-SC₂H₅-C₆H₄ | 110 |
| 395 | CH₃ | —C₂H₄OCH₃ | 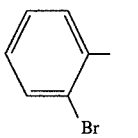 2-Br-C₆H₄ | 164 |
| 396 | CH₃ | —C₂H₄OCH₃ | 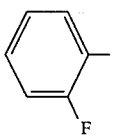 2-F-C₆H₄ | 122 |
| 397 | CH₃ | —C₂H₄OCH₃ | 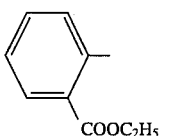 2-COOC₂H₅-C₆H₄ | 92 |
| 398 | CH₃ | —C₂H₄OCH₃ | 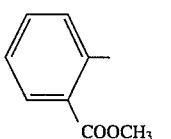 2-COOCH₃-C₆H₄ | 98 |
| 399 | C₂H₅ | —C₂H₄OCH₃ | 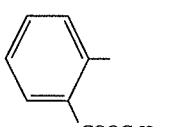 2-COOC₃H₇-n-C₆H₄ | 76 |
| 400 | C₂H₅ | —C₂H₄OCH₃ | 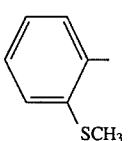 2-SCH₃-C₆H₄ | 88 |
| 401 | C₂H₅ | —C₂H₄OCH₃ | 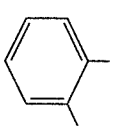 2-CH₃-C₆H₄ | 84 |
| 402 | C₂H₅ | —C₂H₄OCH₃ | 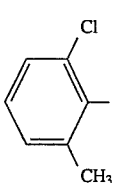 2,6-(CH₃)(Cl)-C₆H₃ | 80 |
| 403 | C₂H₅ | —C₂H₄OCH₃ | 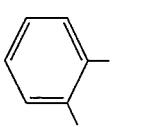 2-OCHF₂-C₆H₄ | 76 |

TABLE 5-continued

Preparation Examples of the compounds of the formula (X)

| Example No. | R² | R³ | Rᵃ | Melting point (°C.) |
|---|---|---|---|---|
| 404 | CH₃ | —C₂H₄OC₂H₅ | 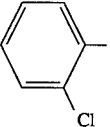 2-Cl-phenyl | 123 |
| 405 | CH₃ | —C₂H₄OC₂H₅ | 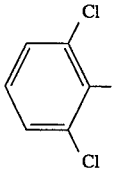 2,6-diCl-phenyl | 122 |
| 406 | CH₃ | —C₂H₄OCH₃ | 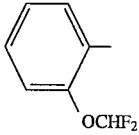 2-OCHF₂-phenyl | 129 |
| 407 | CH₃ | —C₂H₄OCH₃ | 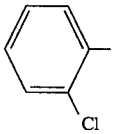 2-Cl-phenyl | 132 |
| 408 | CH₃ | —C₂H₄OCH₃ | 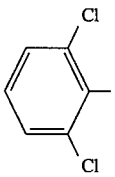 2,6-diCl-phenyl | 122 |
| 409 | C₂H₅ | —C₂H₄OCH₃ | 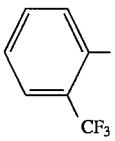 2-CF₃-phenyl | 87 |
| 410 | C₂H₅ | —C₂H₄OCH₃ | 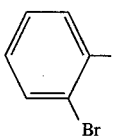 2-Br-phenyl | 78 |
| 411 | C₂H₅ | —C₂H₄OCH₃ | 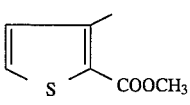 3-COOCH₃-thienyl | 106 |
| 412 | C₂H₅ | —C₂H₄OCH₃ | 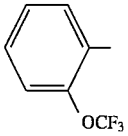 2-OCF₃-phenyl | 75 |
| 413 | C₂H₅ | —C₂H₄OCH₃ | 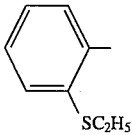 2-SC₂H₅-phenyl | 80 |

TABLE 5-continued

| | Preparation Examples of the compounds of the formula (X) | | | |
|---|---|---|---|---|
| Example No. | R² | R³ | Rª | Melting point (°C.) |
| 414 | C₂H₅ | —C₂H₄OCH₃ | 2-F-C₆H₄ | 78 |
| 415 | C₂H₅ | —C₂H₄OCH₃ | 2-COOC₂H₅-C₆H₄ | 74 |
| 416 | C₂H₅ | —C₂H₄OCH₃ | 2-COOCH₃-C₆H₄ | 78 |
| 417 | C₂H₅ | —C₂H₄OCH₃ | 2-Cl-C₆H₄ | 68 |
| 418 | C₂H₅ | —C₂H₄OCH₃ | 2,3-Cl₂-C₆H₃ | 98 |
| 419 | CH₃ | —C₂H₄OC₃H₇-i | 2-COOC₃H₇-n-C₆H₄ | 88 |
| 420 | CH₃ | —C₂H₄OC₃H₇-i | 2-SCH₃-C₆H₄ | 98 |
| 421 | CH₃ | —C₂H₄OC₃H₇-i | 2-CH₃-C₆H₄ | 106 |
| 422 | CH₃ | —C₂H₄OC₃H₇-i | 2-OCHF₂-C₆H₄ | 106 |
| 423 | CH₃ | —C₂H₄OC₃H₇-i | 2-Cl-3-CH₃-C₆H₃ | 92 |

TABLE 5-continued

Preparation Examples of the compounds of the formula (X)

| Example No. | R² | R³ | Rª | Melting point (°C.) |
|---|---|---|---|---|
| 424 | CH₃ | —C₂H₄OC₃H₇-i | 2-CF₃-phenyl | 136 |
| 425 | CH₃ | —C₂H₄OC₃H₇-i | 3-methyl-2-(COOCH₃)-thiophene | 123 |
| 426 | CH₃ | —C₂H₄OC₃H₇-i | 2-Br-phenyl | 122 |
| 427 | CH₃ | —C₂H₄OC₃H₇-i | 2-OCF₃-phenyl | 116 |
| 428 | CH₃ | —C₂H₄CH(CH₃)OCH₃ | 2-COOC₃H₇-n-phenyl | 78 |
| 429 | CH₃ | —C₂H₄OC₃H₇-i | 2-Cl-phenyl | 126 |
| 430 | CH₃ | —C₂H₄CH(CH₃)OCH₃ | 2-Cl-phenyl | 114 |
| 431 | CH₃ | —CH₂CH(CH₃)OCH₃ | 2-Cl-phenyl | 106 |
| 432 | CH₃ | —CH₂CH(CH₃)OC₂H₅ | 2-Cl-phenyl | 107 |
| 433 | CH₃ | i-C₃H₇ | 2-COOCH₃-phenyl | 145 |

TABLE 5-continued

Preparation Examples of the compounds of the formula (X)

| Example No. | $R^2$ | $R^3$ | $R^a$ | Melting point (°C.) |
|---|---|---|---|---|
| 434 | $CH_3$ | $C_2H_5$ | 2-($OCF_3$)phenyl | 140 (sodium salt) |
| 435 | $CH_3$ | $C_2H_5$ | 2-($CF_3$)phenyl | 140 (sodium salt) |
| 436 | $CH_3$ | $-CH_2CH(CH_3)OCH_3$ | 2,3-di($CH_3$)phenyl | 100 |
| 437 | $CH_3$ | $-CH_2CH(CH_3)OCH_3$ | 2-($OCHF_2$)phenyl | 99 |
| 438 | $CH_3$ | $-CH_2CH(CH_3)OCH_3$ | 2-Cl-3-($CH_3$)phenyl | 86 |
| 439 | $CH_3$ | $-CH_2CH(CH_3)OCH_3$ | 2-($CF_3$)phenyl | 119 |
| 440 | $CH_3$ | $-CH_2CH(CH_3)OCH_3$ | 2-($OCF_3$)phenyl | 119 |
| 441 | $CH_3$ | $-CH_2CH(CH_3)OCH_3$ | 2-F-phenyl | 93 |
| 442 | $CH_3$ | $-CH_2CH(CH_3)OC_2H_5$ | 2-($OCHF_2$)phenyl | 111 |
| 443 | $CH_3$ | $-CH_2CH(CH_3)OC_2H_5$ | 2-($COOCH_3$)phenyl | 113 |

TABLE 5-continued

Preparation Examples of the compounds of the formula (X)

| Example No. | R² | R³ | Rᵃ | Melting point (°C.) |
|---|---|---|---|---|
| 444 | CH₃ | —CH₂CHOC₂H₅ with CH₃ branch | 2-F-phenyl | 86 |
| 445 | CH₃ | —O—(3,4-diCl-phenyl) | 2-COOCH₃-phenyl | 175 |
| 446 | CH₃ | —CH₂CHOCH₃ with C₂H₅ branch | 2-OCHF₂-phenyl | 90 |
| 447 | CH₃ | —CH₂CHOCH₃ with C₂H₅ branch | 2-OCF₃-phenyl | 95 |
| 448 | CH₃ | —CH₂CHOCH₃ with C₂H₅ branch | 2-F-phenyl | 95 |
| 449 | CH₃ | —CH₂CHOCH₃ with C₂H₅ branch | 2-Br-phenyl | 130 |
| 450 | CH₃ | —CH₂CHOCH₃ with CH₃ branch | 2-COOCH₃-phenyl | 77 |
| 451 | CH₃ | —CH₂CHOCH₃ with C₂H₅ branch | 2-Cl-3-CH₃-phenyl | 80 |
| 452 | CH₃ | —CH₂CHOCH₃ with C₂H₅ branch | 2-COOC₃H₇-n-phenyl | 92 |
| 453 | CH₃ | —CH₂CHOC₂H₅ with CH₃ branch | 2-Cl-3-CH₃-phenyl | 74 |

TABLE 5-continued

Preparation Examples of the compounds of the formula (X)

| Example No. | R² | R³ | Rᵃ | Melting point (°C.) |
|---|---|---|---|---|
| 454 | CH₃ | —CH₂CH(CH₃)OC₂H₅ | 2-CF₃-C₆H₄ | 108 |
| 455 | CH₃ | —CH₂CH(CH₃)OC₂H₅ | 2-Br-C₆H₄ | 112 |
| 456 | CH₃ | —CH₂CH(CH₃)OC₂H₅ | 2-OCF₃-C₆H₄ | 103 |
| 457 | CH₃ | CH₃ | 3,4-(OCH₃)₂-C₆H₃ (with H₃CO at 4-position) | 127 |
| 458 | CH₃ | n-C₃H₇ | 2-SCH₃-C₆H₄ | 123 |
| 459 | cyclopropyl | n-C₃H₇ | 2-COOCH₃-C₆H₄ | 128 |
| 460 | CH₃ | CH₃ | 2-SCH₃-C₆H₄ | 179 |
| 461 | CH₃ | CH₃ | 2-SC₂H₅-C₆H₄ | 176 |
| 462 | CH₃ | CH₃ | 2-OCH₃-C₆H₄ | 178 |
| 463 | CH₃ | CH₃ | 2-OC₂H₅-C₆H₄ | 177 |

TABLE 5-continued
Preparation Examples of the compounds of the formula (X)
| Example No. | R² | R³ | Rᵃ | Melting point (°C.) |
|---|---|---|---|---|
| 464 |  | n-C₃H₇ | 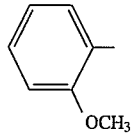 o-OCH₃-C₆H₄ | 94 |
| 465 |  | n-C₃H₇ | 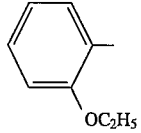 o-OC₂H₅-C₆H₄ | 115 |
| 466 |  | n-C₃H₇ | 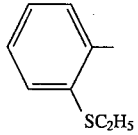 o-SC₂H₅-C₆H₄ | 115 |
| 467 |  | n-C₃H₇ | 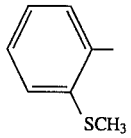 o-SCH₃-C₆H₄ | 119 |
| 468 | CH₃ | CH₃ | 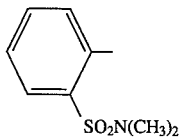 o-SO₂N(CH₃)₂-C₆H₄ | 170 (sodium salt) |
| 469 | CH₃ | CH₃ | 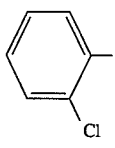 o-Cl-C₆H₄ | 166 |
| 470 | CH₃ | n-C₃H₇ | 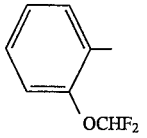 o-OCHF₂-C₆H₄ | 124 |
| 471 | CH₃ | n-C₃H₇ | 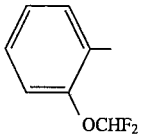 o-OCHF₂-C₆H₄ | 178 (sodium salt) |
| 472 | CH₃ | CH₃ | 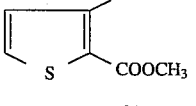 | 192 |
| 473 | CH₃ | CH₃ | 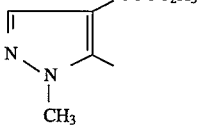 | 160 |

TABLE 5-continued

Preparation Examples of the compounds of the formula (X)

| Example No. | $R^2$ | $R^3$ | $R^a$ | Melting point (°C.) |
|---|---|---|---|---|
| 474 | $CH_3$ | n-$C_3H_7$ | 2-$CF_3$-$C_6H_4$ | 149 |
| 475 | $CH_3$ | n-$C_3H_7$ | 2-$OCF_3$-$C_6H_4$ | 131 |
| 476 | $CH_3$ | n-$C_3H_7$ | 2-$OCH_3$-$C_6H_4$ | 156 |
| 477 | $CH_3$ | n-$C_3H_7$ | 2-$OC_2H_5$-$C_6H_4$ | 131 |
| 478 | $CH_3$ | n-$C_3H_7$ | 2-Cl-3-$CH_3$-$C_6H_3$ | 150 |
| 479 | $CH_3$ | n-$C_3H_7$ | 2,3-$Cl_2$-$C_6H_3$ | 171 |
| 480 | $CH_3$ | n-$C_3H_7$ | 2-$CH_3$-$C_6H_4$ | 147 |
| 481 | $CH_3$ | n-$C_3H_7$ | 2-$SC_2H_5$-$C_6H_4$ | 111 |
| 482 | $CH_3$ | n-$C_3H_7$ | 2,5-($OCH_3$)$_2$-$C_6H_3$ | 124 |

TABLE 5-continued

| | Preparation Examples of the compounds of the formula (X) | | | |
|---|---|---|---|---|
| Example No. | R² | R³ | Rᵃ | Melting point (°C.) |
| 483 | CH₃ | n-C₃H₇ | 2-OC₂H₅, 4-OC₂H₅ phenyl | 112 |
| 484 | cyclopropyl | n-C₃H₇ | 2-COOC₂H₅ phenyl | 118 |
| 485 | cyclopropyl | n-C₃H₇ | 2-COOC₃H₇-n phenyl | 116 |
| 486 | cyclopropyl | n-C₃H₇ | 2-CF₃ phenyl | 103 |
| 487 | cyclopropyl | n-C₃H₇ | 2-OCF₃ phenyl | 81 |
| 488 | cyclopropyl | n-C₃H₇ | 2-CH₃ phenyl | 114 |
| 489 | cyclopropyl | n-C₃H₇ | 2-Cl phenyl | 120 |
| 490 | cyclopropyl | n-C₃H₇ | 2-Br phenyl | 107 |
| 491 | cyclopropyl | n-C₃H₇ | 2-Cl, 3-CH₃ phenyl | 143 |

TABLE 5-continued
Preparation Examples of the compounds of the formula (X)
| Example No. | R² | R³ | Rᵃ | Melting point (°C.) |
|---|---|---|---|---|
| 492 |  | n-C₃H₇ | 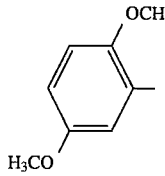 | 132 |
| 493 | CH₃ | CH₃ | 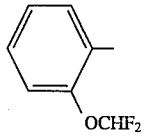 | 121 (sodium salt) |
| 494 | CH₃ | n-C₃H₇ | 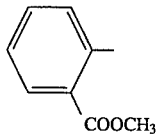 | 188 (sodium salt) |
| 495 | CH₃ | CH₃ | 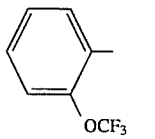 | 175 (sodium salt) |
| 496 |  | n-C₃H₇ | 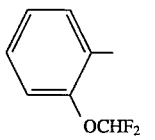 | 111 |
| 497 | CH₃ | 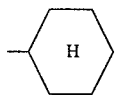 | 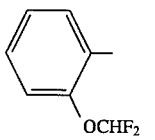 | 108 |
| 498 | CH₃ | i-C₄H₉ | 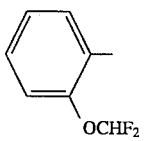 | 129 |
| 499 | CH₃ | 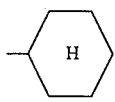 | 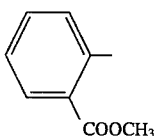 | 117 |
| 500 | CH₃ | i-C₄H₉ | 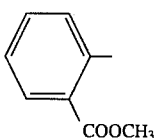 | 96 |
| 501 | CH₃ | —CH₂CF₃ | 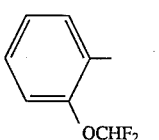 | |

STARTING SUBSTANCES OF THE FORMULA (II)

Example (II-1)

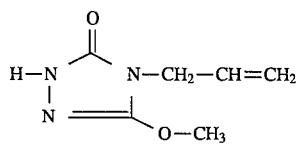

A mixture of 5.0 g (0.02 mol) of 1-phenoxycarbonyl-4-allyl-O-methyl-isosemicarbazide and 30 ml of toluene is refluxed for 15 minutes and subsequently concentrated under a water pump vacuum. The residue is triturated with diethyl ether/petroleum ether, and the product which has been obtained in crystalline form is isolated by filtration with suction.

2.0 g (64% of theory) of 4-allyl-5-methoxy-2,4-dihydro-3H-1,2,4-triazol-3-one of melting point 111° C. are obtained.

Example (II-2)

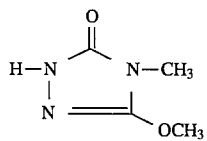

50.2 g (0.33 mol) of phenyl hydrazinoformate and 36.6 g (0.33 mol, 93% strength) of trimethyl iminocarabonate are heated to 60° C. in 100 ml of absolute o-dichlorobenzene, and the mixture is stirred for 2 hours, during which process a clear mixture is stirred for 2 hours, during which process a clear solution is formed. In the course of two hours, it is heated to 120° C., during which process methanol distilled off. A vacuum is applied carefully, during which process more methanol and finally phenol distil off. Further distillation results in a fraction which solidifies in the receiving vessel in crystalline form.

After recrystallisation from toluene, 7.0 g (0.054 mol, 16% of theory) of 4-methyl-5-methoxy-2,4-dihydro-3H-1,2,4-triazol-3-one of melting point 142°–144° C. are obtained in the form of colourless crystals. This compound in known from F. Arndt et al, Rev. faculte. Sci. Univ. Istanbul, 13A, 127 (1948).

Other examples of compounds of the formula (II) which can be prepared analogously to Examples (II-1) and (II-2) are those listed in Table 6 below.

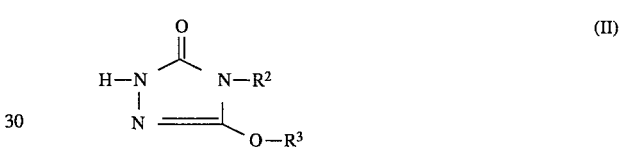

TABLE 6

Examples of the starting substances of the formula (II)

| Example No. | $R^2$ | $R^3$ | Melting point (°C.) |
|---|---|---|---|
| II-3 | $CH_3$ | phenyl | 163 |
| II-4 | $CH_3$ | $C_3H_7$ | 72 |
| II-5 | cyclopropyl | $CH_3$ | 149 |
| II-6 | cyclopropyl | $C_2H_5$ | 130 |
| II-7 | $CH(CH_3)_2$ | $CH_3$ | 80–81 |
| II-8 | $C_2H_5$ | $CH_3$ | (b.p.: 120° C. at 1.5 mbar) |
| II-9 | $C_3H_7$ | $CH_3$ | (b.p.: 130–150° C. at 1.5 mbar) |
| II-10 | $CH_3$ | $C_4H_9$ | 152–153 |
| II-11 | $(CH_2)_3OCH_3$ | $CH_3$ | 84–85 |
| II-12 | $CH_3$ | $C_2H_5$ | (b.p.: 140–150° C. at 1.5 mbar) |
| II-13 | $CH(CH_3)_2$ | $C_2H_5$ | 66–67 |
| II-14 | $C_3H_7$ | $C_2H_5$ | (b.p.: 140–150° C. at 1.5 mbar) |
| II-15 | $CH_2=CH-CH_2$ | $C_2H_5$ | (b.p.: 150° C. at 1.5 mbar) |
| II-16 | cyclopropyl | n-$C_3H_7$ | 100 |

TABLE 6-continued

Examples of the starting substances of the formula (II)

| Example No. | R² | R³ | Melting point (°C.) |
|---|---|---|---|
| II-17 | CH₃ | 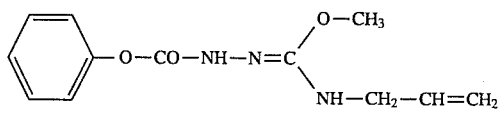 | 106 |
| II-18 | CH₃ | i-C₃H₇ | 134 |
| II-19 | CH₃ | —C₂H₄OC₂H₅ | 90 |
| II-20 | CH₃ | —C₂H₄OCH₃ | 125 |
| II-21 | C₂H₅ | —C₂H₄OCH₃ | 94 |
| II-22 | C₂H₅ | —C₂H₄OC₃H₇-i | 92 |
| II-23 | CH₃ | —CH₂CH₂CHOCH₃ (with CH₃) | 73 |
| II-24 | CH₃ | —CH₂CHOCH₃ (with CH₃) | (Oil) |
| II-25 | CH₃ | —CH₂CHOC₂H₅ (with CH₃) | (Oil) |
| II-26 | CH₃ | —CH₂CHOCH₃ (with C₂H₅) | 37 |
| II-27 | CH₃ | —CH₂CH(CH₃)₂ | (amorphous) |
| II-28 | CH₃ | —CH₂CH=CH₂ | 69 |
| II-29 | CH₃ | —CH₂CH₂CH(CH₃)₂ | 82 |
| II-30 | CH₃ | (cyclohexyl-H) | 116 |
| II-31 | CH₃ | —CH₂C(CH₃)₃ | 130 |

INTERMEDIATES OF THE FORMULA (XVII)

Example (XVII-1)

C₆H₅—O—CO—NH—N=C(O—CH₃)(NH—CH₂—CH=CH₂)

A mixture of 30.4 g (0.2 mol) of phenyl hydrazinoformate, 26.0 g (0.2 mol) of methyl N-allyl-iminocarbonate and 150 ml of methanol is stirred for 12 hours at 20° C. and subsequently concentrated under a water pump vacuum. The residue is triturated with diethyl ether/ethanol (1/1 by vol.), and the crystalline product is isolated by filtration with suction.

11.0 g (22% of theory) of 1-phenoxycarbonyl-4-allyl-O-methyl-isosemicarbazide of melting point 114° C. are obtained.

Other examples of compounds of the formula (IX) which can be prepared analogously to Example (IX-1) are those listed in Table 5 below.

R⁴—O—CO—NH—N=C(O—R³)(NH—R²)  (XVII)

TABLE 7

Examples of the compounds of the formula (XVII)

| Example No. | R² | R³ | R⁴ | Melting point (°C.) |
|---|---|---|---|---|
| XVII-2 | CH₃ | CH₃ | 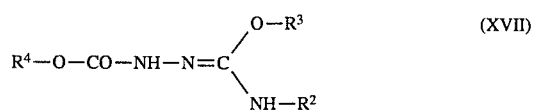 | 123 |
| XVII-3 | C₂H₅ | CH₃ | C₂H₅ | 137 |
| XVII-4 | CH₃ | CH₃ | CH₃ | 134 |
| XVII-5 | CH₃ | CH₃ | C₂H₅ | 135 |

TABLE 7-continued

Examples of the compounds of the formula (XVII)

| Example No. | R² | R³ | R⁴ | Melting point (°C.) |
|---|---|---|---|---|
| XVII-6 | C₂H₅ | CH₃ | 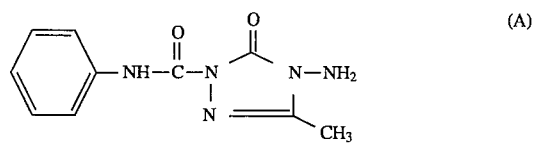 | 133–134 |

USE EXAMPLES

In the Use Examples, the following compound (A) is used as comparison substance:

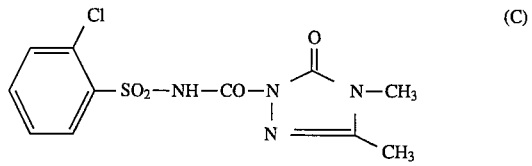
(A)

4-amino-5-methyl-2-phenylaminocarbonyl-2,4-dihydro-3-H-1,2,4-triazol-3-one (disclosed in EP-A 294,666).

Example A

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1000 l of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds of Preparation Examples 1 and 2.

Example B

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds combined with good tolerance by crop plants such as, for example, barley, is shown, for example, by the compound of Preparation Example 2.

USE EXAMPLES

In the second Use Examples, the following compound (C) is used as comparison substance:

(C)

2-(2-chloro-phenylsulphonylaminocarbonyl)-4,5-dimethyl-2,4-dihydro-3H-1,2,4-triazol-3-one (disclosed in EP-A 341,489).

Example C

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, a considerably more powerful action against weeds than the known compound (C) is shown, for example, by the compounds of Preparation Examples 1, 2, 3, 53, 54, 55, 56, 57, 58, 64, 65 and 67, while having, in some cases, good crop plant compatibility.

Example D

| | Pre-emergence test |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a considerably more powerful action against weeds than the known compound (C) is shown, for example, by the compounds of Preparation Examples 2, 54 and 69, while having, in some cases, good crop plant compatibility.

It will be understood that the specification and examples are illustrative but not limitative of the present invention and that other embodiments within the spirit and scope of the invention will suggest themselves to those skilled in the art.

What is claimed is:

1. A triazolinone of the formula $$\text{(II)}$$

in which $R^2$ represents amino, or represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxycarbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or $C_1$–$C_7$ cycloalkyl-$C_1$–$C_6$-alkyl or represents phenyl-$C_1$–$C_3$- alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxy-carbonyl, or represents $C_1$–$C_4$-alkylamino which is optionally substituted by fluorine, cyano, $C_1$–$C_4$-alkoxy or $C_1$–$C_4$-alkoxy-carbonyl, or represents $C_3$–$C_6$-cycloalkylamino or di-($C_1$–$C_4$-alkyl)-amino, and $R^3$ represents $C_1$–$C_6$-alkyl which is optionally substituted by fluorine, chlorine, bromine, cyano, $C_3$–$C_6$-cycloalkyl, $C_1$–$C_4$-alkoxy or $C_1$–$C_4$-alkoxycarbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkyl-sulphinyl, $C_1$–$C_4$-alkylsulphonyl and/or $C_1$–$C_4$-alkoxy-carbonyl, provided that when $R^2$ is methyl, $R^3$ cannot be methyl.

2. A triazolinone according to claim 1, wherein $R^2$ represents $C_1$–$C_3$ alkyl, $C_2$–$C_3$ alkenyl or $C_3$–$C_6$-cycloalkyl and $R^3$ represents $C_1$–$C_6$ alkyl, $C_2$–$C_6$ alkenyl or $C_2$–$C_6$ alkynyl.

3. A triazolinone according to claim 1, wherein $R^2$ represents methyl or cyclopropyl and $R^3$ represents methyl, ethyl, n-propyl, i-propyl, n-butyl or allyl.

4. A triazolinone according to claim 1, wherein $R^2$ represents ethyl or allyl and $R^3$ represents methyl, ethyl, n-propyl, i-propyl, n-butyl and allyl.

5. A triazolinone according to claim 1, wherein

| | |
|---|---|
| $R^2 = CH_3$ | $R^3 = C_2H_5$ |
| $R^2 = CH_3$ | $R^3 = C_3H_7n$ |
| $R^2 = CH_3$ | $R^3 = C_3H_7i$ |
| $R^2 = CH_3$ | $R^3 = $ allyl |
| $R^2 = CH_3$ | $R^3 = C_4H_9n$ |
| $R^2 = $ cyclopropyl | $R^3 = CH_3$ |
| $R^2 = $ cyclopropyl | $R^3 = C_2H_5$ |
| $R^2 = $ cyclopropyl | $R^3 = C_3H_7n$ |
| $R^2 = $ cyclopropyl | $R^3 = C_3H_7i$ |
| $R^2 = $ cyclopropyl | $R^3 = $ allyl. |

* * * * *

UNITED STATES PATENT AND TRADEMARK OFFICE
CERTIFICATE OF CORRECTION

PATENT NO.  : 5,541,337
DATED       : July 30, 1996
INVENTOR(S) : Muller, et al.

It is certified that error appears in the above-indentified patent and that said Letters Patent is hereby corrected as shown below:

Title Page , item [22],   Related U.S. Application Data: Line 3 after " 757,785 " delete " Nov 11, 1991 " and substitute -- Sep. 11, 1991 --

Signed and Sealed this

Thirty-first Day of March, 1998

Attest:

BRUCE LEHMAN

Attesting Officer           Commissioner of Patents and Trademarks